(12) United States Patent
Zhang et al.

(10) Patent No.: US 10,655,173 B2
(45) Date of Patent: May 19, 2020

(54) SPATIAL AND CELLULAR MAPPING OF BIOMOLECULES IN SITU BY HIGH-THROUGHPUT SEQUENCING

(71) Applicants: THE BROAD INSTITUTE, INC., Cambridge, MA (US); Massachusetts Institute of Technology, Cambridge, MA (US)

(72) Inventors: Feng Zhang, Cambridge, MA (US); Joshua Asher Weinstein, Cambridge, MA (US); Aviv Regev, Cambridge, MA (US)

(73) Assignees: THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 15/030,154

(22) PCT Filed: Oct. 17, 2014

(86) PCT No.: PCT/US2014/061077
§ 371 (c)(1),
(2) Date: Apr. 18, 2016

(87) PCT Pub. No.: WO2015/058052
PCT Pub. Date: Apr. 23, 2015

(65) Prior Publication Data
US 2016/0265046 A1  Sep. 15, 2016

Related U.S. Application Data

(60) Provisional application No. 61/892,766, filed on Oct. 18, 2013.

(51) Int. Cl.
*C12Q 1/6874* (2018.01)
*C12Q 1/6844* (2018.01)

(52) U.S. Cl.
CPC ......... *C12Q 1/6874* (2013.01); *C12Q 1/6846* (2013.01)

(58) Field of Classification Search
CPC ............................ C12Q 1/6874; C12Q 1/6846
USPC .......................................................... 506/9
See application file for complete search history.

(56) References Cited

U.S. PATENT DOCUMENTS

| | | |
|---|---|---|
| 4,971,903 A | 11/1990 | Hyman |
| 5,202,231 A | 4/1993 | Drmanac et al. |
| 5,210,015 A | 5/1993 | Gelfand et al. |
| 5,403,708 A | 4/1995 | Brennan et al. |
| 5,445,934 A | 8/1995 | Fodor et al. |
| 5,525,464 A | 6/1996 | Drmanac et al. |
| 5,547,839 A | 8/1996 | Dower et al. |
| 5,695,940 A | 12/1997 | Drmanac et al. |
| 5,795,782 A | 8/1998 | Church et al. |
| 5,902,723 A | 5/1999 | Dower et al. |
| 2010/0240101 A1 | 9/2010 | Lieberman |
| 2012/0208714 A1* | 8/2012 | Stegger ............... C12Q 1/689 506/9 |
| 2014/0073013 A1* | 3/2014 | Gorman ................ B01L 7/52 435/91.2 |
| 2016/0265046 A1 | 9/2016 | Zhang et al. |

FOREIGN PATENT DOCUMENTS

| | | |
|---|---|---|
| WO | 9323564 A1 | 11/1993 |
| WO | 9639154 A1 | 12/1996 |
| WO | 9813523 A1 | 4/1998 |
| WO | 9828440 A1 | 7/1998 |
| WO | 9703211 A1 | 1/1999 |
| WO | 2012/083225 A2 | 6/2012 |
| WO | 2012/140224 A1 | 10/2012 |
| WO | 2014047556 A1 | 3/2014 |
| WO | 2015058052 A1 | 4/2015 |

OTHER PUBLICATIONS

Bagasra et al. (Nature Protocols, vol. 2, No. 11, 2007, pp. 2782-2795). (Year: 2007).*
International Preliminary Report on Patentabiity and Written Opinion Report dated Apr. 19, 2016, which issued during prosecution of International Application No. PCT/US2014/061077.
European Office Action for European Patent Application No. 14792688.5, dated Feb. 6, 2018, 7.
European Office Action for European Patent Application No. 14792688.5, dated Dec. 20, 2018, 9.
European Office Action for European Patent Application No. 14792688.5, dated Apr. 21, 2017, 6.
Begley, "A new 'DNA microscope' peers deep inside living cells", Stat, Jun. 20, 2019, 4.
Chung, et al., "Structural and Molecular Interrogation of Intact Biological Systems", Nature, vol. 497, No. 7449, May 16, 2013, 332-337.
Dekosky, et al., "High-Throughput Sequencing of the Paired Human Immunoglobulin Heavy and Light Chain Repertoire", Nature Biotechnology, vol. 31, No. 2, Feb. 2013, 166-169.
Fan, "This Radical New DNA Microscope Reimagines the Cellular World", Singularity Hub, Jul. 2, 2019, 6.

(Continued)

*Primary Examiner* — Karla A Dines
(74) *Attorney, Agent, or Firm* — Johnson, Marcou, Isaacs & Nix, LLC; F. Brent Nix, Esq.; Rachel D. Rutledge, Esq.

(57) ABSTRACT

The present invention relates to molecular microscopy or volumetric imaging by proximal unique molecular identifiers ("UID") reaction ("VIPUR") microscopy methods to record the cellular co-localization and/or spatial distributions of arbitrary nucleic acid sequences, or other biomolecules tagged with nucleic sequences. The method involves one or both of two DNA sequence-components such as an α-UID, which may identify the targeted sequences-of-interest themselves and/or spatial beacons relative to which their distances are measured, and a- β-UID, which labels α-UID association events.

12 Claims, 15 Drawing Sheets

Specification includes a Sequence Listing.

(56) References Cited

OTHER PUBLICATIONS

Glaser, et al., "Puzzle Imaging: Using Large-Scale Dimensionality Reduction Algorithms for Localization", Plos One, Jul. 20, 2015, 23.

Lee, et al., "Highly Multiplexed Subcellular RNA Sequencing In Situ", Science, vol. 343, No. 6177, Mar. 21, 2014, 1360-1363.

Leslie, "Researchers Use DNA to Take Pictures of Cells", Technology, Jun. 20, 2019, 2.

Sheikh, "DNA Microscope Sees 'Through the Eyes of the Cell'", The New York Times,, Jun. 20, 2019, 4.

Turchaninova, "Pairing of T-Cell Receptor Chains via Emulsion PCR", European Journal of Immunology, vol. 43, 2013, 2507-2515.

Van Der Maaten, et al., "Visualizing Data Using t-SNE", Journal of Machine Learning Research, vol. 9, 2008, 2579-2605.

Weinstein, et al., "DNA Microsopy: Optics-Free Spatio-Genetic Imaging by a Stand-Alone Chemical Reaction", Cell, vol. 178, Jun. 27, 2019, 30.

International Search Report dated Feb. 5, 2015, which issued during prosecution of International Application No. PCT/US2014/061077.

Embleton, et al. "IN-cell PCR from mRNA: amplifying and linking the rearranged immunoglobulin heavy and light chain V-genes within single cells" Nucleic Acids Research, Jan. 1992, 20(15):3831-3837.

Shiroguchi, et al. "Digitial RNA sequencing minimizes sequence-dependent bias and amplification noise with optimized single-molecule barcodes" Proceedings of The National Academy of Sciences, Jan. 2012. 109(4):1347-1352.

Nuovo, et al. "Co-labeling Using In Situ PCR: A Review" Journal of Histochemistry & Cytochemistry, Nov. 2001, 49(11):1329-1339.

\* cited by examiner

FIG. 3B

SEQUENCE LISTING

```
<160> NUMBER OF SEQ ID NOS: 24

<210> SEQ ID NO 1
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (22)..(28)
<223> OTHER INFORMATION: a, c, t, g, unknown or other
<220> FEATURE:
<221> NAME/KEY: modified_base
<222> LOCATION: (31)..(37)
<223> OTHER INFORMATION: a, c, t, g, unknown or other
<220> FEATURE:
<221> NAME/KEY: modified_base
<222> LOCATION: (40)..(46)
<223> OTHER INFORMATION: a, c, t, g, unknown or other
```

-continued

<400> SEQUENCE: 1
gacgtgtgct cttccgatct tnnnnnnnat nnnnnnnatn nnnnnnttac tccttggagg        60
ccatgt                                                                   66

<210> SEQ ID NO 2
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (22)..(28)
<223> OTHER INFORMATION: a, c, t, g, unknown or other
<220> FEATURE:
<221> NAME/KEY: modified_base
<222> LOCATION: (31)..(37)
<223> OTHER INFORMATION: a, c, t, g, unknown or other
<220> FEATURE:
<221> NAME/KEY: modified_base
<222> LOCATION: (40)..(46)
<223> OTHER INFORMATION: a, c, t, g, unknown or other

<400> SEQUENCE: 2
gacgtgtgct cttccgatct tnnnnnnnat nnnnnnnatn nnnnnntctt gaagttcacc        60
ttgatgc                                                                  67

<210> SEQ ID NO 3
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (22)..(28)
<223> OTHER INFORMATION: a, c, t, g, unknown or other
<220> FEATURE:
<221> NAME/KEY: modified_base
<222> LOCATION: (31)..(37)
<223> OTHER INFORMATION: a, c, t, g, unknown or other
<220> FEATURE:
<221> NAME/KEY: modified_base
<222> LOCATION: (40)..(46)
<223> OTHER INFORMATION: a, c, t, g, unknown or other

<400> SEQUENCE: 3
gacgtgtgct cttccgatct tnnnnnnnat nnnnnnnatn nnnnnnccat ggtcttcttc        60
tgcatt                                                                   66

<210> SEQ ID NO 4
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (23)..(29)
<223> OTHER INFORMATION: a, c, t, g, unknown or other
<220> FEATURE:
<221> NAME/KEY: modified_base
<222> LOCATION: (32)..(38)

<223> OTHER INFORMATION: a, c, t, g, unknown or other
<220> FEATURE:
<221> NAME/KEY: modified_base
<222> LOCATION: (41)..(47)
<223> OTHER INFORMATION: a, c, t, g, unknown or other

<400> SEQUENCE: 4
ttgaggtgtc ctaaacttac gcnnnnnnna tnnnnnnnat nnnnnnncta gagaagtggg    60
gtggctttt                                                           69

<210> SEQ ID NO 5
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
tggtctcaac atatcgcatc ctgggctaca ctgagcacca gg                       42

<210> SEQ ID NO 6
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
tggtctcaac atatcgcacc atcttcttca aggacgacgg caac                     44

<210> SEQ ID NO 7
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
tggtctcaac atatcgcagt tcatgtacgg ctccaaggcc tac                      43

<210> SEQ ID NO 8
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
tggcttcaaa ttcacgcaaa ctggaacggt gaaggtgaca gcag                     44

<210> SEQ ID NO 9
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
gttcagacgt gtgctcttcc gatct                                              25

<210> SEQ ID NO 10
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
atgagtggct tcaaattcac gc                                                 22

<210> SEQ ID NO 11
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(23)
<223> OTHER INFORMATION: a, c, t, g, unknown or other
<220> FEATURE:
<221> NAME/KEY: modified_base
<222> LOCATION: (26)..(30)
<223> OTHER INFORMATION: a, c, t, g, unknown or other

<400> SEQUENCE: 11
tattcccatg gcgcgccann nnnatnnnnn ttgaggtgtc taaacttac gc                  52

<210> SEQ ID NO 12
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(23)
<223> OTHER INFORMATION: a, c, t, g, unknown or other
<220> FEATURE:
<221> NAME/KEY: modified_base
<222> LOCATION: (26)..(30)
<223> OTHER INFORMATION: a, c, t, g, unknown or other

<400> SEQUENCE: 12
ggcgcgccat gggaataann nnnatnnnnn tggagtggtc tcaacatatc gc                 52

<210> SEQ ID NO 13
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 13
ccctacacga cgctcttccg atctctccat cctaaaagcc accccacttc tcta              54

<210> SEQ ID NO 14
<211> LENGTH: 66
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14
caagcagaag acggcatacg agatattcct ctgtgactgg agttcagacg tgtgctcttc    60
cgatct                                                               66

<210> SEQ ID NO 15
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
tttttttttt tattcccatg gcgcgcca                                       28

<210> SEQ ID NO 16
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
tttttttttt ggcgcgccat gggaataa                                       28

<210> SEQ ID NO 17
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
aatgatacgg cgaccaccga gatctacact ctttccctac acgacgctct tccgatctag    60 ccacccact tctcta                                                     76

<210> SEQ ID NO 18
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (25)..(32)
<223> OTHER INFORMATION: a, c, t, g, unknown or other

<400> SEQUENCE: 18
caagcagaag acggcatacg agatnnnnnn nngtgactgg agttcagacg tgtgctcttc    60
cgatct                                                               66

<210> SEQ ID NO 19
<211> LENGTH: 143
```

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
taaaagccac cccacttctc tactaaatat ctaccgattc ccttgcgtaa gtttaggaca      60
cctcaatgca cattaagctg gcgcgccatg ggaataaaag atataaaaat ggagtggtct     120
caacatatcg catcctgggc tac                                             143

<210> SEQ ID NO 20
<211> LENGTH: 143
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20
taacctggat ggagctcatg cggatgttac tccttggagg ccatgtgggc catgaggtcc      60
accaccctgt tgctgtagcc aaattcgttg tcataccagg aaatgagctt gacaaagtgg     120
tcgttgaggg caatgccagc ccc                                             143

<210> SEQ ID NO 21
<211> LENGTH: 142
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21
gtggcttcaa attcacgcat cctgggctac actgagcacc aggtggtctc ctctgacttc      60
aacagcgaca cccactcctc cacctttgac gctggggctg gcattgccct caacgaccac     120
tttgtcaagc tcatttcctg gt                                              142

<210> SEQ ID NO 22
<211> LENGTH: 142
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22
taagccactc atatctctgc gttcatcgat catattccca tggcgcgcca acagcatcca      60
cccagaagat tgaggtgtcc taaacttacg ctacatgaat agaatggatg gtgggtttac     120
tccttggagg ccatgtgggc ca                                              142

<210> SEQ ID NO 23
<211> LENGTH: 142
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

```
<400> SEQUENCE: 23
ggtgtcctaa acttacgcaa gatagattaa cactatttct gacttactcc ttggaggcca      60
tgtgggccat gaggtccacc accctgttgc tgtagccaaa ttcgttgtca taccaggaaa     120
tgagcttgac aaagtggtcg tt                                              142

<210> SEQ ID NO 24
<211> LENGTH: 142
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24
tggacacctc aatcttctgg cgacatccca ctggcgcgcc atgggaataa tactaattag      60
ttcagagata tgagtggctt caaattcacg catcctgggc tacactgagc accaggtggt    120
ctcctctgac ttcaacagcg ac                                              142
```

SPATIAL AND CELLULAR MAPPING OF BIOMOLECULES IN SITU BY HIGH-THROUGHPUT SEQUENCING

RELATED APPLICATIONS AND/OR INCORPORATION BY REFERENCE

The present application is filed pursuant to 35 U.S.C. § 371 as a U.S. National Phase Application of International Patent Application Number PCT/US2014/061077, which was filed on Oct. 17, 2014, which was published as PCT Publication No. WO2015/058052 on Apr. 23, 2015, which claims the benefit of and priority to U.S. provisional patent application Ser. No. 61/892,766 filed Oct. 18, 2013.

FEDERAL FUNDING LEGEND

This invention was made with government support under Grant No. MH100706 awarded by the National Institutes of Health. The Government has certain rights in the invention.

The foregoing applications, and all documents cited therein or during their prosecution ("appln cited documents") and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to molecular microscopy or volumetric imaging by proximal unique molecular identifiers ("UID") reaction ("VIPUR") microscopy methods, in particular recording spatial distributions of DNA or RNA, or molecular targets tagged with DNA or RNA, in non-dissociated cells or biological tissue at single-cell or subcellular resolution by randomized barcoding of DNA or cDNA before and during in situ amplification.

SEQUENCE LISTING

The instant application contains a Sequence Listing which has been submitted electronically in ASCII format and is hereby incorporate by reference in its entirety. Said ASCII copy created on Apr. 14, 2016, is named 46783.01.2033_SL.txt and is 10 kb in size.

BACKGROUND OF THE INVENTION

Cellular phenotype is commonly characterized by mRNA expression profiling. However, in heterogeneous populations of cells, profiling cell populations in bulk discards all information pertaining to the associations of specific mRNA transcripts in individual cells. In immunoglobulin-producing lymphocytes, for example, pooled sequencing results in the separate characterizations of immunoglobulin heavy- and light-chains, peptides whose co-expression within a cell determines an immunoglobulin's antigen-specificity. To resolve this, heavy- and light-chain mRNA produced by individual lymphocytes may be made to associate in the sequence of a polymerase chain reaction (PCR) product (Embleton M J, et al. Nucleic Acids Res. 1992 Aug. 11; 20(15): 3831-3837). In this method, cells from two clonal populations were fixed and permeabilized, their heavy- and light-chain mRNA reverse transcribed to cDNA, and the cDNA amplified by PCR with primers containing reverse-complementary overhangs which allowed heavy- and light-chain PCR product to cross-link during the reaction. The fidelity of chimeric heavy/light chain PCR product to the original intracellular co-localization could then be verified either using fluorescent primers using fluorescence microscopy or by screening of bacterial colonies transfected with chimeric PCR product. (Embleton M J, et al. Nucleic Acids Res. 1992 Aug. 11; 20(15): 3831-3837).

High-throughput sequencing can identify large numbers of heavy- and light-chain variable regions ($V_H$ and $V_L$) in a given B-cell repertoire, but information about endogenous pairing of heavy and light chains is lost after bulk lysis of B-cell populations. A way to retain this pairing information involves depositing single B cells ($>5 \times 10^4$ capacity per experiment) in a high-density microwell plate (125 pl/well) and lysing (DeKosky B J, et al. Nat Biotechnol. 2013 February; 31(2):166-9). mRNA is then captured on magnetic beads, reverse transcribed and amplified by emulsion $V_H:V_L$ linkage PCR and the linked transcripts are analyzed by Illumina high-throughput sequencing (DeKosky B J, et al. Nat Biotechnol. 2013 February; 31(2):166-9).

RNA sequencing (RNA-Seq) is a powerful tool for transcriptome profiling, but is hampered by sequence-dependent bias and inaccuracy at low copy numbers intrinsic to exponential PCR amplification. To mitigate these complications to allow truly digital RNA-Seq, a large set of barcode sequences is added in excess, and nearly every cDNA molecule is uniquely labeled by random attachment of barcode sequences to both ends (Shiroguchi K, et al. Proc Natl Acad Sci USA. 2012 Jan. 24; 109(4):1347-52). After PCR, paired-end deep sequencing is applied to read the two barcodes and cDNA sequences. Rather than counting the number of reads, RNA abundance is measured based on the number of unique barcode sequences observed for a given cDNA sequence (Shiroguchi K, et al. Proc Natl Acad Sci USA. 2012 Jan. 24; 109(4):1347-52). The barcodes may be optimized to be unambiguously identifiable, even in the presence of multiple sequencing errors. This method allows counting with single-copy resolution despite sequence-dependent bias and PCR-amplification noise, and is analogous to digital PCR but amendable to quantifying a whole transcriptome (Shiroguchi K, et al. Proc Natl Acad Sci USA. 2012 Jan. 24; 109(4):1347-52).

Prior technologies, such as those described above, to identify the contents of individual cells required their dissociation so that they may be analyzed individually. In the case of structurally fragile cell types, such as neurons, this generally required severing whole cell parts, such as dendrites that branch from the main cell body.

Fluorescence in situ sequencing, or FISSEQ, is a method that allows the acquisition of mRNA/cDNA sequences directly from within cell monolayers or whole mount embryos (Lee J H et al. Science. 2014 Mar. 21; 343(6177): 1360-3). mRNA transcripts are reverse-transcribed into cDNA and fixed to the cellular matrix. mRNA is degraded, and the cDNA subsequently circularized so that polonies comprising long repeats of cDNA sequence may be formed by rolling circle amplification (RCA). SOLiD sequencing (sequencing by oligonucleotide ligation and detection) is then used to read out 30 bp reads that allow comparison with reference gene transcripts. In order to resolve individual transcripts, signals are suppressed so that polonies are sufficiently sparse to be distinguished from one another optically. FISSEQ requires high-quality optics for each sample to be analyzed. Moreover, because of trade-offs between a microscope's depth-of-field and its imaging resolution, samples must be properly arranged on a two-dimensional plane to be analyzed.

Citation or identification of any document in this application is not an admission that such document is available as prior art to the present invention.

SUMMARY OF THE INVENTION

The invention solves the challenge of sequencing DNA or RNA, or identifying molecular targets tagged with DNA or RNA, in non-dissociated fixed cells or sectioned or intact biological tissue at single-cell or subcellular resolution.

The present invention relates to randomized barcoding of DNA or cDNA before and during in situ amplification. Random barcoding of DNA/cDNA before in situ amplification creates a UID (unique molecular identifier) for DNA/cDNA template molecules. Cross-linking of DNA-amplification products is accompanied by random-barcoding of cross-linking events, giving each such event its own UID as well. Sequencing template- and cross-link-addresses and combining them generates a hierarchy of physical co-localization among groups of template DNA/cDNA molecules in the biological sample.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 3A-B illustrates the Target-Target embodiment of molecular microscopy. Here, cross-linked products comprise repeats of the same structural unit. Target-Target molecular microscopy follows the same experimental flow as Beacon-Target Molecular Microscopy, except that beacon gene transcripts are not amplified by their own primer sets, and two small sequences, (14) and (15), are inserted into reverse-transcription and second-strand synthesis primers, respectively. Sequences (14) and (15) permit separate amplification of the two overlapping sides of the final cross-linked amplicons product (vi and viii). During library preparation, because both sides of the amplicon are identical, only the blocking-oligo technique (TABLE 1, Turchaninova M A et al. Eur J Immunol. 2013 September; 43(9):2507-15) may be used to suppress late-stage overlap-extension. The two amplification reactions are compared and matched based on shared β-UID sequences (FIG. 7).

FIG. 10A illustrates the data-flow. Here, UID's are counted if they associate with at least 2 sequence-reads.

DETAILED DESCRIPTION OF THE INVENTION

Figure 1:
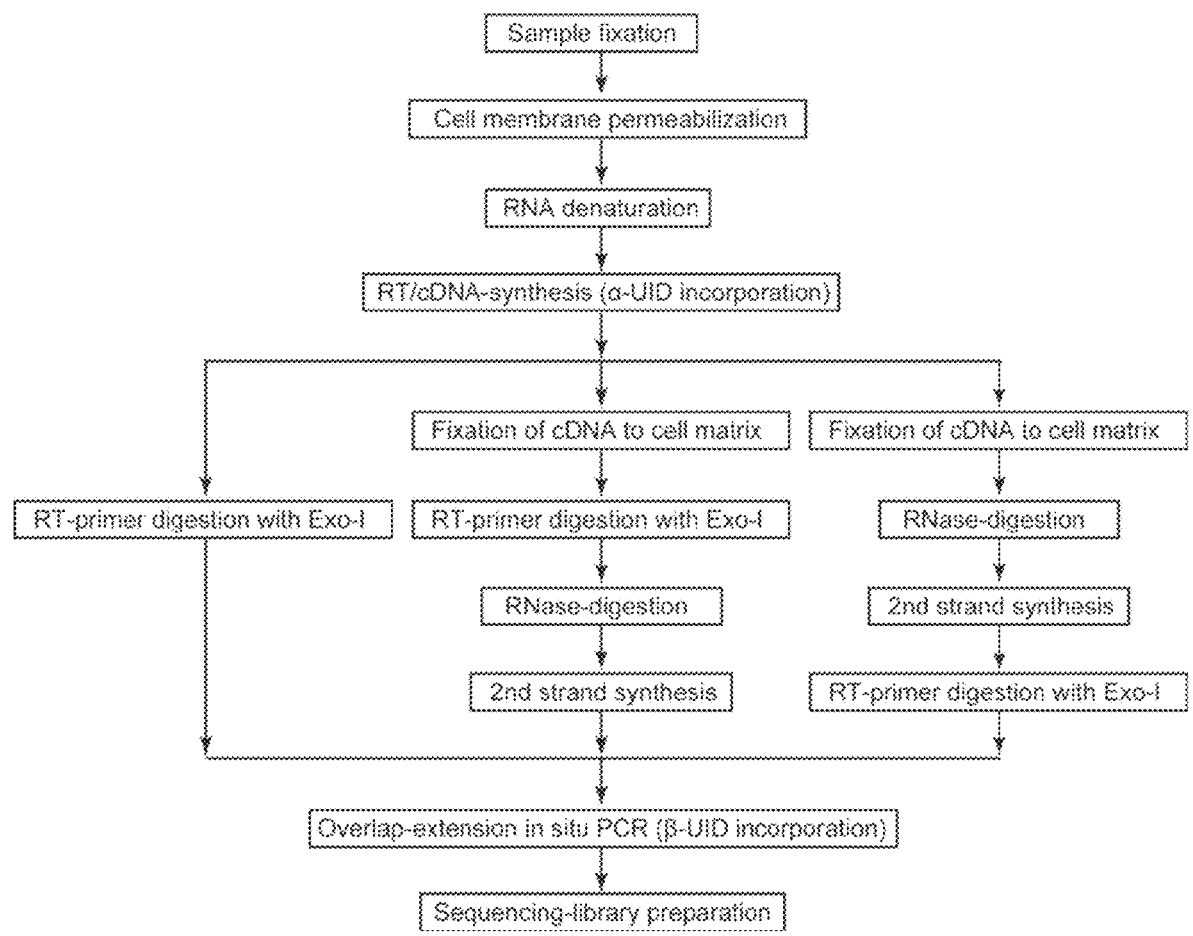
FIG. 1 depicts a flowchart of the method's experimental structure. Following sample fixation and membrane permeabilization, RNA is denatured (chemically under acid-treatment and/or by heating). Reverse transcription (cDNA synthesis) incorporates primers with randomized α-UID nucleotides flanked by reverse-adapters. For lower background, or for random (whole transcriptome) priming, amino-allyl dUTP is incorporated into the cDNA backbone so that the cDNA itself may be immobilized, RNA degraded, and second DNA strand synthesized (see FIG. 4 for further detail). Exonuclease I treatment follows cDNA synthesis in order to degrade all residual primers used for reverse transcription. Overlap-extension in situ PCR links α-UID-labeled amplicons together, and incorporates randomized β-UID nucleotides between them. Reaction products are then prepared as libraries for NGS (Next Generation Sequencing).

As used herein, α-UID (unique address) refers to random or highly diverse nucleic acid sequences included to barcode biological targets (eg mRNA transcripts).

As used herein, β-UID refers to random or highly diverse nucleic acid sequences included to barcode cross-linking events between PCR products.

Molecular microscopy, which may be interchangeably referred to as volumetric imaging by proximal unique molecular identifiers ("UID") reaction ("VIPUR") microscopy aims to record the cellular co-localization and/or spatial distributions of arbitrary DNA/RNA sequences, or other biomolecules tagged with DNA/RNA sequences. It achieves this with one or both of two sequence-components. The first, the α-UID, uniquely identifies the targeted sequences-of-interest themselves, so that after amplification, all reads coming from that target-sequence can be identified as originating from a single template DNA/RNA molecule. The second sequence-component, the β-UID, functions to associate two or more α-UID's, either as a spatial beacon existing independently of α-UID association, or generated by the α-UID cross-linking process itself. Both α-UID's and β-UID's must be either unique themselves, unique in the context of the final data-set, or recognizable as non-unique such that they may be discarded or otherwise prevented from compromising downstream analysis.

Together, when they can be associated, α-UID's and β-UID's together provide enough information to reconstruct the spatial distribution of DNA/cDNA-sequences if certain criteria are met: (1) The measured frequencies of association between pairs of α-UID sequences, whether these associations are direct or through association with specific β-UID's, must be a function of distance between the original α-UID template molecules; (2) If the association of two α-UID's is indirect, via their association with β-UID's, then these α-UID's must either both associate with a specific β-UID or associate with distinct β-UID's that are associated via an additional UID that physically links them, and may be amplified, sequenced, and analyzed in the context of the final data-set; (3) If cross-linking occurs over short-distances, such as through a physical linker, then preferentially high frequencies of cross-linking events between identical α-UID's and/or β-UID's (in embodiments where self-to-self pairing among UID's occurs) must be mitigated. Alternatively, if cross-linking occurs over long-distances, such as by diffusion, resultant low cross-linking frequencies between identical or originally-nearby α-UID's and/or β-UID's must be mitigated; (4) If β-UID's have (effectively) finite diversity, such that the same β-UID occurs multiple times in sample-prep independently, then each α-UID-tagged DNA/cDNA molecule must bind/hybridize multiple times to nearby β-UID's in order to sample the local population of β-UID's instead of single β-UID's individually.

As used herein, random or pre-defined nucleic acid sequences drawn from a pool of may be utilized in characterizing the UID's of the present invention, the UID's relate to and encompass an entire spectrum of sequence-types ranging from perfectly random to perfectly defined. A key feature of the UID is that it satisfies the following diversity criterion. As used herein, a pool of pre-defined nucleic acid sequences may refer to replacing random nucleotides with a mixture of defined sequences that are either (a) so diverse themselves so that assigning one per target- or beacon-biomolecule uniquely labels each or (b) sufficiently diverse so that in combination with the identity of the target- or beacon-biomolecule, they uniquely label each. A pool of pre-defined nucleic acid sequences used as a UID may encompass computationally designed error correcting sequences in addition to non-error-correcting sequences.

In one embodiment of α-UID delivery, cDNA molecules may be individually tagged with α-UID's using randomized-oligonucleotides of at least 10 bp in length, inserted between a gene-specific or gene-nonspecific (poly-dN or poly-dT) and universal reverse-adapter regions of the reverse-transcription primer. By adding amino-allyl dUTP at a low concentration to the reverse-transcription reaction, and then fixing the sample, cDNA's may be covalently bound to the cell matrix. If cDNA is fixed to the cellular matrix, second-strand synthesis may then be used to incorporate universal forward adapters before in situ amplification. This permits annealing of a highly multiplexed, or randomized, primer set, for coverage of a greater number of genes. If cDNA is not fixed, second-strand synthesis must be performed at the same stage as in situ amplification. Prior to in situ amplification, exonuclease I is used to degrade residual primers. These steps are illustrated in FIG. 1, FIG. 2A, FIG. 3A, and FIG. 4A.

In a second embodiment of α-UID delivery, epitope-targeting antibodies conjugated to RNA, single-stranded DNA, or double-stranded DNA, in each case comprised of sequences to indicate antibody or epitope identity, may be used to stain cells or a tissue sample. α-UID delivery, by the addition of 10 or more randomized nucleotides to the antibody-conjugated nucleic acid sequence, may take place either before or after sample-staining. Universal adapter sequences, flanking both the α-UID and the antibody-identifier sequence, are included for amplification in the downstream reaction.

Figure 3A:
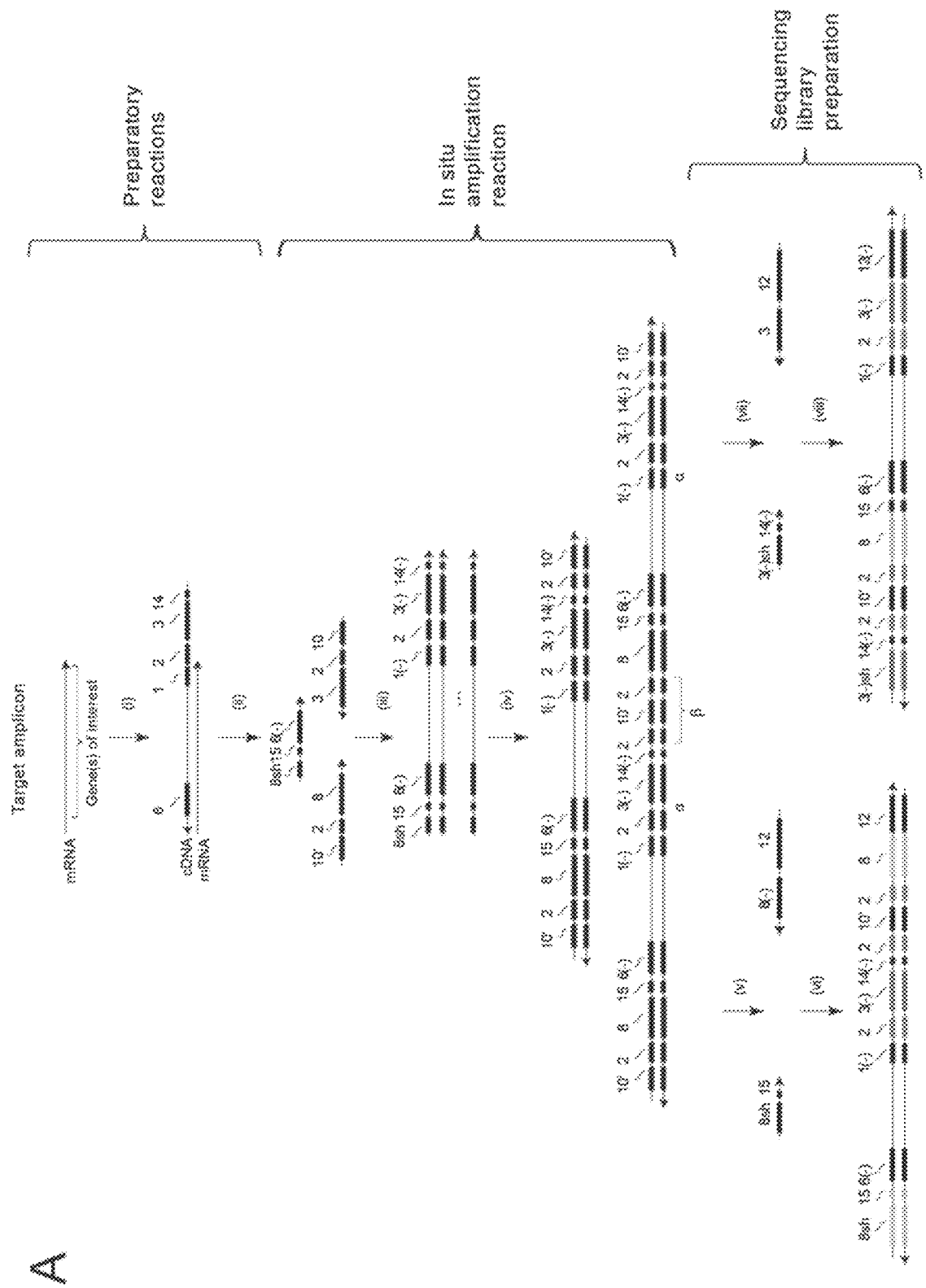
Figure 3B:
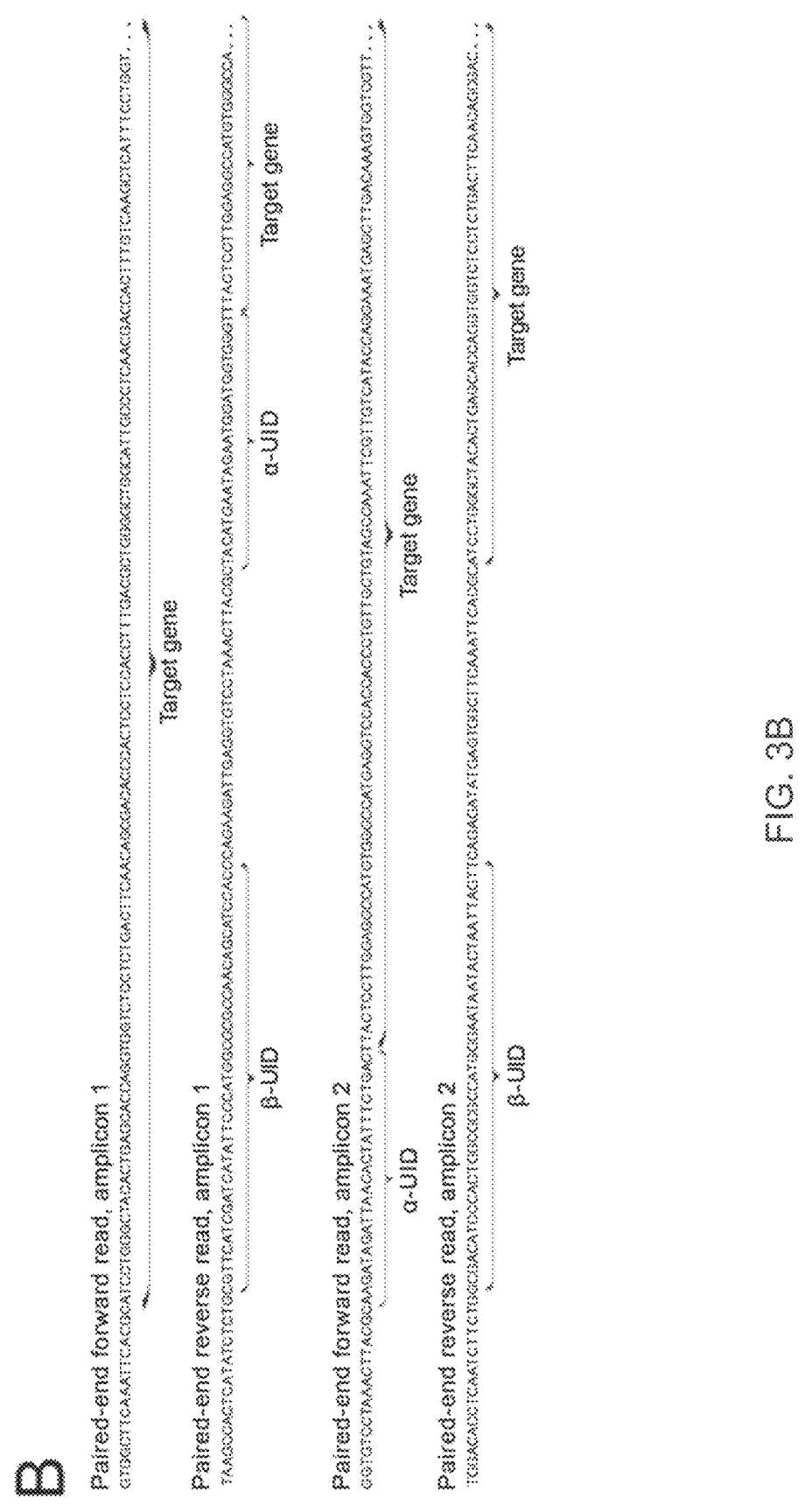
Figure 4A:
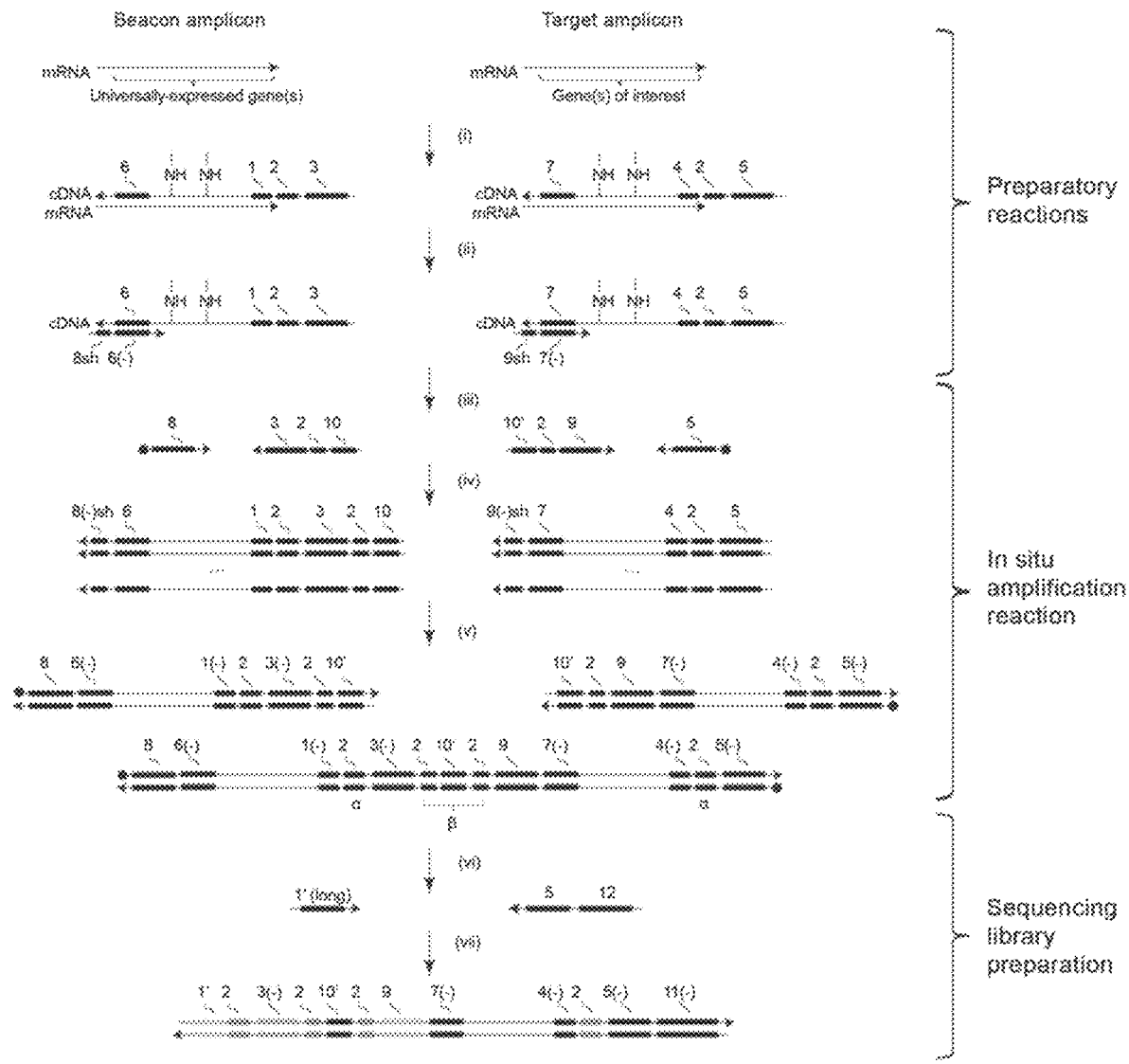
FIG. 4 illustrates an embodiment of Beacon-Target Molecular Microscopy wherein second strand synthesis is performed in advance of overlap-extension in situ PCR. cDNA is synthesized with dNTP and amino-allyl dUTP. NH2-groups are then fixed to the cell matrix (i) in order to immobilize the molecule following RNA digestion (Lee J H et al. Science. 2014 Mar. 21; 343(6177):1360-3). The subsequent second-strand synthesis anneals primers to gene sequences (6) and (7) for beacon- and target-amplicons, respectively. At the 5' end of each, the short sequences (8sh) and (9sh) allow for linear amplification illustrated previously in FIG. 2 and FIG. 3.
Figure 4B:
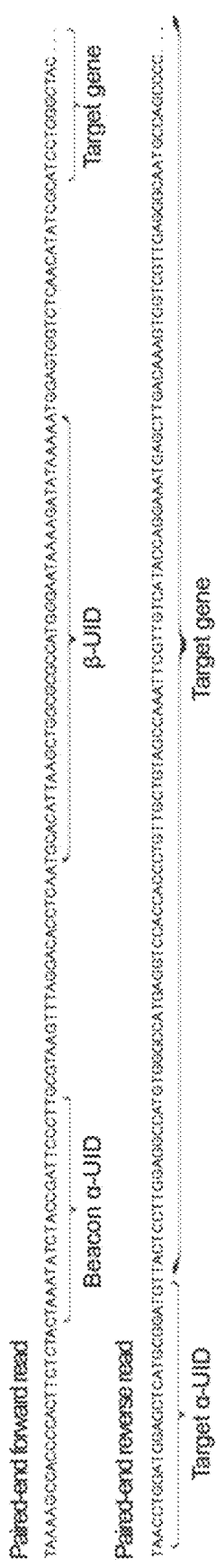

In a third embodiment of α-UID delivery, α-UID's incorporated into DNA amplicons by either of the first two embodiments (reverse-transcription or antibody-labeling) may be flanked by either of two distinct types of adapter-pairs. The first of these adapter-pair types, designated "target" adapters, amplify biological sequences meant to be mapped in space. The second of these adapter-pair types, designated "beacon" adapters, amplify endogenous or exogenously-introduced amplicons. A sample may be prepared in this way to include either only amplicons labeled with target-adapters or both amplicons labeled with target-adapters and amplicons labeled with beacon-adapters. In the former case, called "Target-Target Molecular Microscopy" or "Target-Target VIPUR Microscopy", α-UID-labeled target-amplicons are mapped entirely relative to one another (FIG. 3). In the latter case, called "Beacon-Target Molecular Microscopy" or "Beacon-Target VIPUR Microscopy", α-UID-labeled target-amplicons are mapped relative to α-UID-labeled beacon-amplicons (FIG. 2 and FIG. 4).

Figure 2A:
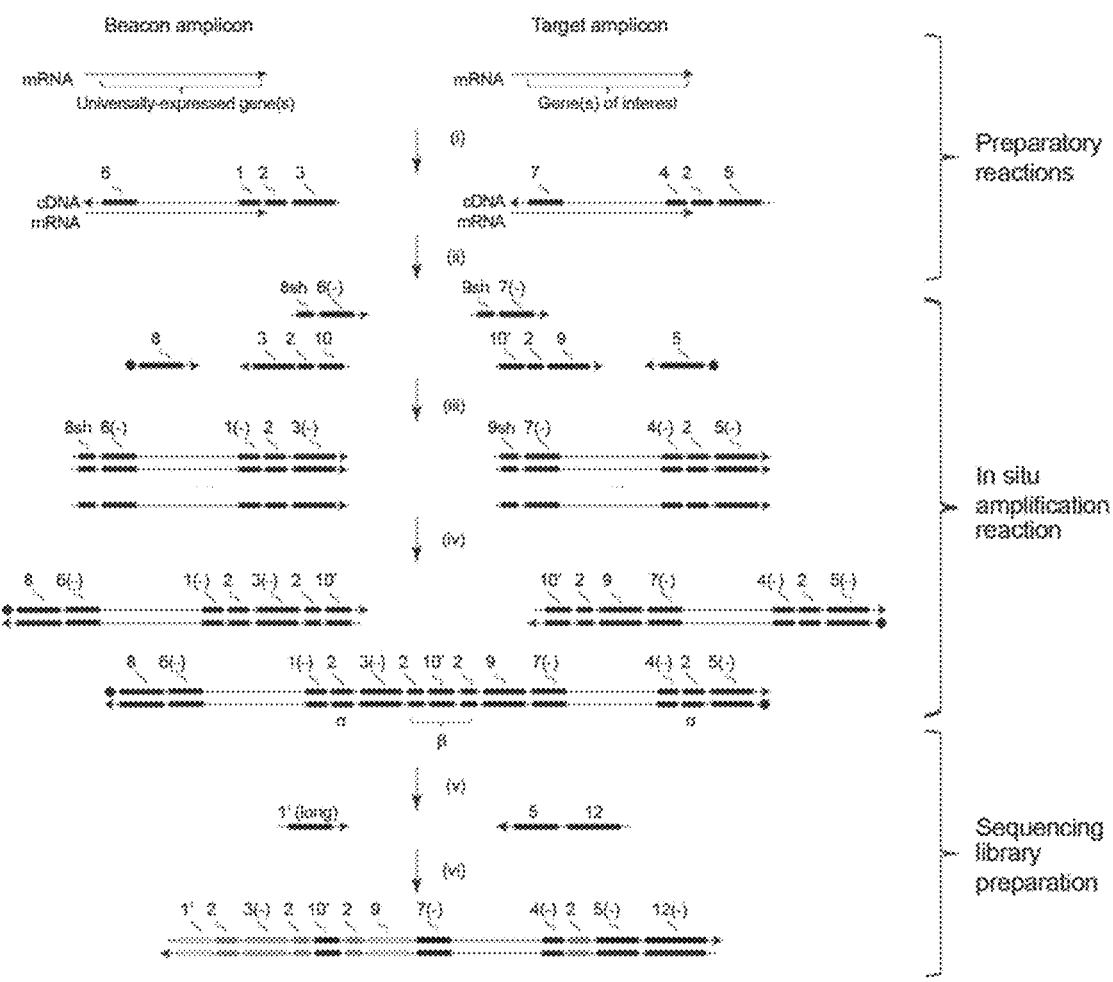
FIG. 2A-B illustrates the Beacon-Target Molecular Microscopy experimental flow for gene-specific amplification. Following cell fixation and permeabilization (i), cDNA synthesis proceeds for beacon-transcripts with primers containing a beacon-specific sequence (1), a randomized α-UID sequence (2), and a universal handle (3). The cDNA product extends to include a new beacon-specific priming site (6). cDNA from target-transcripts is synthesized with primers containing a target-specific sequence (4), a randomized α-UID sequence (2), and a universal handle (5), with the product containing a new target-specific priming site (7). Following exonuclease I treatment (ii), the in situ overlap-extension PCR reaction is prepared. Second-strand synthesis primers specific to priming sites (6) and (7) are added at a low concentration. These primers contain, on their 5'-ends, short universal handles (8sh) and (9sh) with low melting temperatures. PCR primers include a primer containing the universal handle (8) subsuming the short handle (8sh) and a primer containing the universal handle (9) subsuming the short handle (9sh), the latter containing on its 5' end an overlap-extension adapter sequence (10') and randomized nucleotides (2). PCR primers further include a primer containing the universal handle (5) and a primer containing the universal handle (3) in addition to randomized nucleotides (2) and the overlap-extension adapter sequence (10), reverse-complementary to (10'), on its 5' end. Initially, DNA amplification (iii) proceeds by thermocycling with a high primer-annealing temperature above the maximum for priming the short sequences (8sh) and (9sh). This results in a linear (ie constant) amplification rate of both beacon and target amplicons). Subsequently, primer-annealing temperatures are lowered so that (8sh) and (9sh) may be primed, resulting in exponential amplification (iv). The reaction results in overlap-extension between amplicons molecules, leading to both the monomeric and dimeric products shown. In these products, α-UID's retain information on template molecules of origin, and newly incorporated randomized nucleotides comprise β-UID's that label unique cross-linking (ie overlap-extension) events. After reaction product elution (v), sequencing library preparations are prepared by amplifying from universal handles (1) and (5) to incorporate NGS adapters (vi). During this reaction, overlap-extension suppression is performed using the techniques listed in TABLE 1, individually or in combination. Example forward- and reverse-reads from the final NGS product are shown.
Figure 2B:
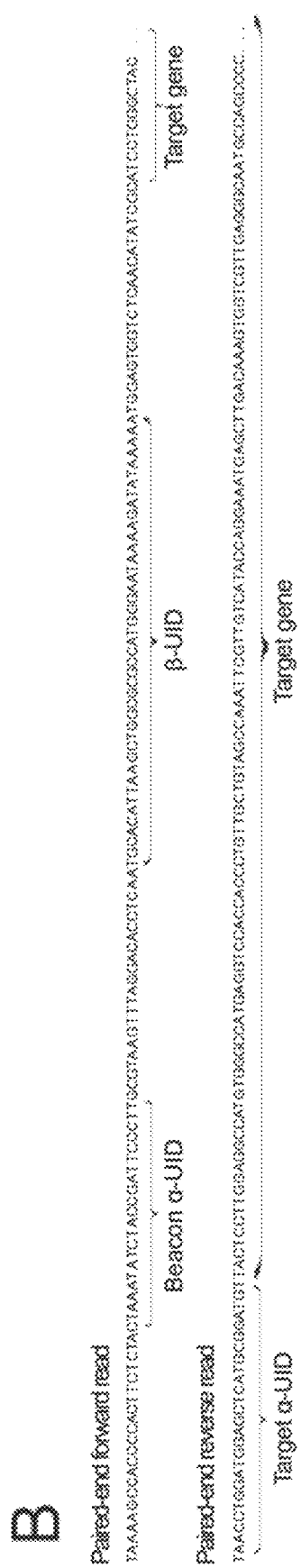

In one embodiment of β-UID delivery, reverse- and forward-primers, with (inner) 3'-adapters targeting α-UID-tagged DNA, include reverse-complementary (outer) 5'-adapter sequences. Through overlap and extension during PCR of α-UID-tagged DNA; these outer-adapter sequences cause amplification products to cross-link. β-UID's are delivered by including randomized nucleotides in between the inner- and outer-adapter sequences (FIGS. 1-3, TABLE 2). While these randomized nucleotides turn over each time the amplicon is newly primed, a cross-linking event will incorporate and fix the included randomized nucleotides in the middle of the new cross-link-amplicon. These newly fixed randomized nucleotides comprise the new β-UID sequence. In Beacon-Target Molecular Microscopy, primers are designed (TABLE 2) to allow β-UID's to only form between target-amplicon/beacon-amplicon pairs (FIGS. 2 and 4). These dimers may then be amplified, however formation of additional dimers from residual monomeric products must be suppressed. This may be done by any one of several methods (TABLE 1), or several of these methods in combination. Because the dimer product is asymmetric, phosphorothioate groups may be included to protect only the exterior 5'-ends of the dimer product (while monomeric products are left unprotected at one end). Subsequently, T7 exonuclease and exonuclease I treatment eliminates all products with at least one unprotected end. Biotin pull-down may be used, as may 3'-capped primers that add nucleotides to free overlap-extension adapters (Turchaninova M A et al. Eur J Immunol. 2013 September; 43(9):2507-15). The sequence read-out is illustrated in FIG. 2B. In Target-Target Molecular Microscopy, β-UID's form between pairs of target-amplicons that have been amplified with the same adapters (FIG. 3). Dimer amplicons may then be amplified, however formation of additional dimers from residual monomeric products must be suppressed. This is done by using 3'-capped primers to block free overlap-extension adapters (TABLE 1). Amplification in this way is performed in two distinct reactions with sequence adapters (FIG. 3A). The sequence read-out is illustrated in FIG. 3B.

In a second embodiment of β-UID delivery, reverse- and forward-primers, with (inner) 3'-adapters targeting α-UID-tagged DNA may be delivered on solid supports of known size such that the distances between pairs of α-UID-tagged DNA can be calculated. The delivery of these β-UID tags may be via nanoparticles or other bio-molecules of known size. Delivery of β-UIDs in this manner can also serve to localize regions using the beacon strategy where individual nanoparticles contain an additional unique label providing the ability to disambiguate locations based on the uniqueness of the nanoparticle β-UID label.

Inference of DNA/cDNA position in the original sample may be performed using any low-dimensionality embedding of the UID association matrix that is robust to experimental noise. In particular, the embedding algorithm must prioritize information about the close proximity between UID's, since this is the information most directly provided by the data derived from the invention.

In one embodiment of DNA/cDNA position inference, t-SNE embedding is used. t-SNE minimizes the Kullback-Leibler (KL)-distance measure between functions of the observed distance and the estimated distance in a low- (2 or 3) dimensional space (LJP van der Maaten and G E Hinton. Journal of Machine Learning Research 9(November):2579-2605, 2008). To apply this method to the current invention, β-UID diversity, $n_{ij}$ for beacon i and target j is converted into a unit-normalized joint-distribution, $P_{ij}$. This is done by setting $$P_{i|j} = n_{ij}/\Sigma_i n_{ij}, P_{j|i} = n_{ij}/\Sigma_j n_{ij}, \text{ and}$$

$$P_{ij} = (P_{i|j} + P_{j|i})/\Sigma_{ij}(P_{i|j} + P_{j|i}).$$

Afterward, defining a t-distributed function of estimated positions $\vec{y}_i$ $$Q_{ij} = \frac{\left(1 + \|\vec{y}_i - \vec{y}_j\|^2\right)^{-1}}{\sum_{k\ell}\left(1 + \|\vec{y}_k - \vec{y}_\ell\|^2\right)^{-1}}$$

allows us to define the KL distance $$D_{KL} = \sum_{ij} P_{ij} \log P_{ij}/Q_{ij}$$

Figure 11:
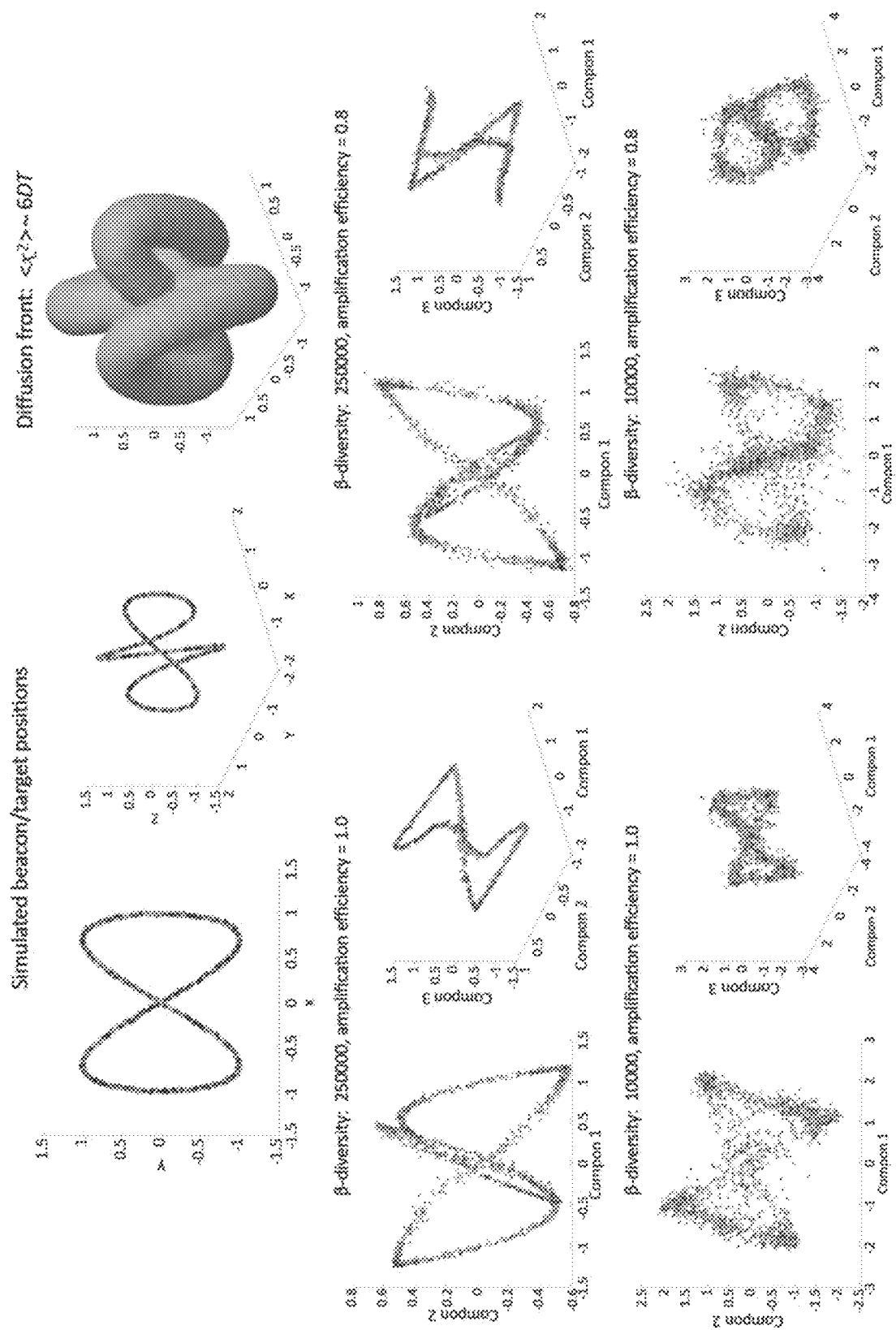
FIG. 11 plots the three-dimensional t-SNE visualization of 1000 simulated beacon positions and 1000 simulated target positions. Simulations proceeded for T=28 rounds of simulated PCR, with diffusion constant D=0.001 (where time was in units of PCR cycles). The front, indicating the mean distance of migration from each UID at the final time-point, is illustrated. After allowing reaction products to diffuse and amplify stochastically (with per-cycle amplification efficiency ≤1), cross-linking events (β-UID diversity) were detected at the indicated counts. Simulated sequencing was performed at a depth of 1000000 reads per sample.
Figure 12:
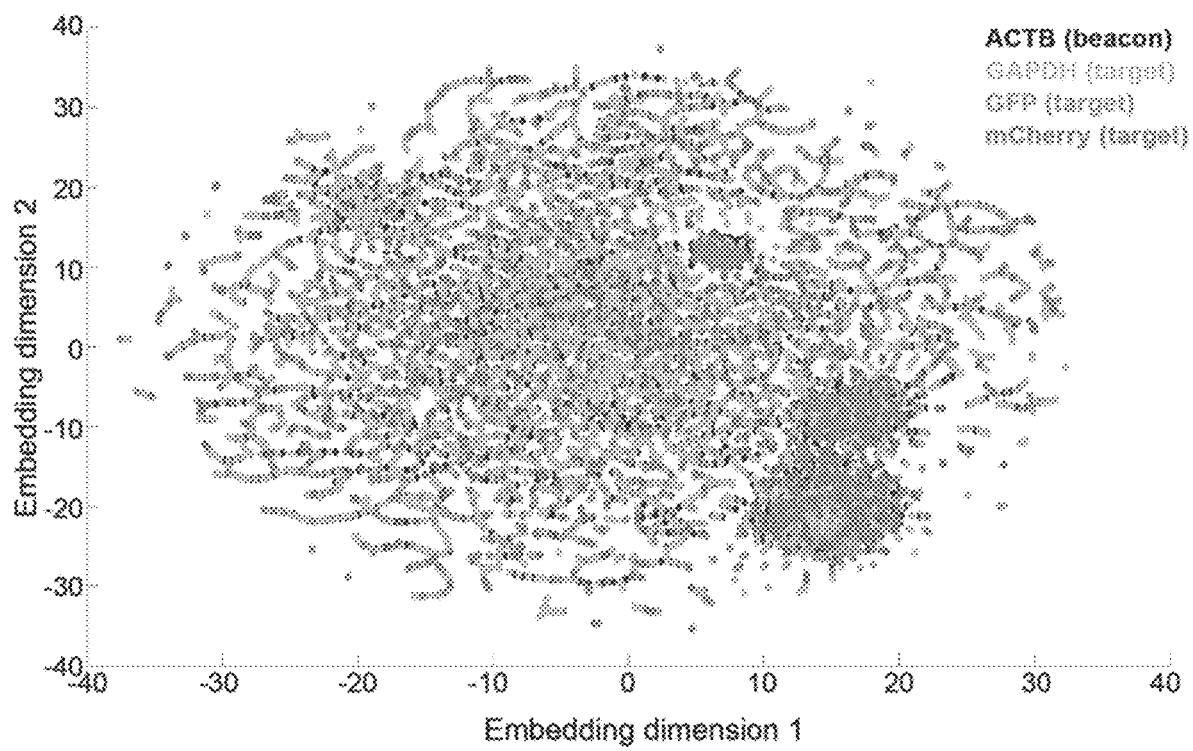
FIG. 12 plots the two-dimensional t-SNE visualization of Beacon-Target Molecular Microscopy experiment performed in PEG hydrogel, in which 10 cycles of linear amplification followed by 22 cycles of PCR (exponential amplification) were performed. ACTB transcripts are used as beacon molecules and GAPDH, GFP, and mCherry transcripts are used as target molecules. Cells expressing GFP or mCherry always expressed one and not the other. Each dot represents an α-UID cluster associated with at least 2 β-UID's (both derived using the EASL algorithm) each having at least 2 reads. GFP and mCherry transcripts among large modules are found to co-localize with the universally expressed GAPDH and ACTB genes, but not with each other, indicating spatial information was encoded into, and decoded from, the sequencing library.

Its minimization provides solutions to $\vec{y}_i$. Simulated data-sets are illustrated in FIG. 11, and its application to real data from GFP- and mCherry-expressing cells is illustrated in FIG. 12.

Figure 10A:
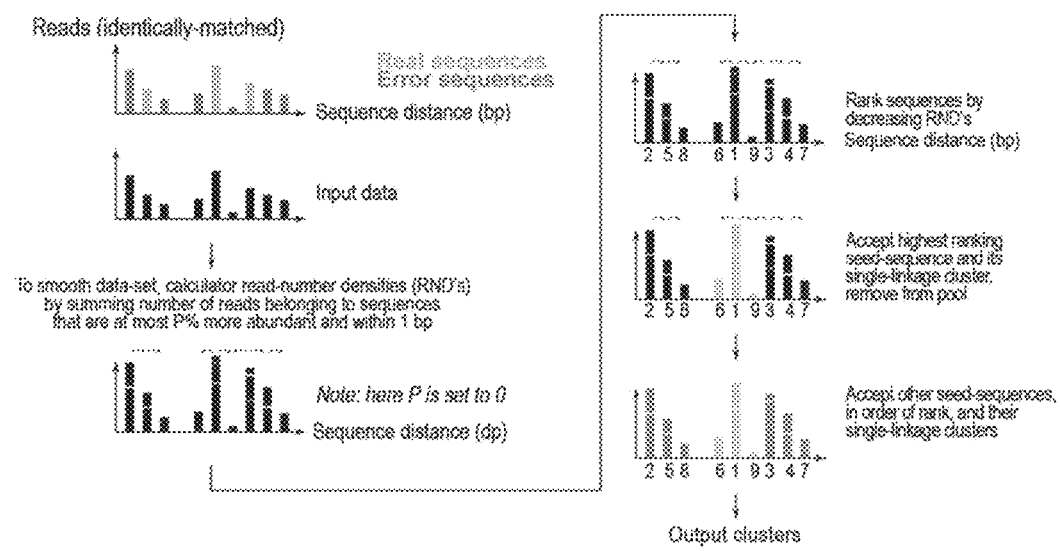
FIG. 10A-B illustrates UID-clustering by the EASL algorithm.

The present application also relates to an UID-clustering algorithm, here called Extended Abundance Single Linkage, or EASL, clustering (FIG. 10).

The algorithm initiates by grouping every UID (of the same type and within the same data-set) by perfect identity, and read-abundance is assigned to each UID sequence by the number of reads identically grouping in this manner.

Each pair of UID's (of the same type and within the same data-set) is compared in an un-gapped alignment. UID i (directionally) links to UID j if and only if the read-abundance of UID i is greater than or equal to the factor (1+P/100), where P is a non-negative percentage parameter, multiplied by the read-abundance of UID j.

Read number densities, or RND's, are calculated for each UID sequence by summing read-abundances belonging both to the sequence itself and all sequences it links to.

The UID with the largest RND initiates clustering as the first cluster-seed. All UID's to which this seed links by the aforementioned criterion are accepted into its cluster, all UID's to which these newly accepted UID's link are accepted as well, and so on. In this way, single-linkage clusters are formed in which the linkages themselves are not always bidirectional.

Once no further assignments can be made to the first cluster, the algorithm proceeds to the UID with the next largest RND that has not already been accepted into a cluster. The same cluster-assembly proceeds among all un-assigned UID's.

When no un-assigned UID's remain, the algorithm terminates.

The question of how much potential UID diversity (or how many randomized UID nucleotides) is necessary may be reduced to the so-called "birthday-problem". Given a UID length l, the probability that two randomly-drawn UID's will match (assuming uniform base-distributions) is $P_0(l)=4^{-l}$. Similarly, the probability that there will be another UID within 1 bp is $$P_{\leq 1}(\ell) = \frac{1 + 3\ell}{4^\ell}$$

The probability that no 2 UID's out of N will overlap in this way is

Prob(0 overlap)=$(1-P_{\leq 1}(l))(1-2P_{\leq 1}(l)) \ldots (1-(N-1)P_{\leq 1}(l))$ Define $N_{crit}(l)$ through the relation $$\tfrac{1}{2}=(1-P_{\leq 1}(l))(1-2P_{\leq 1}(l)) \ldots (1-(N_{crit}(l)-1)P_{\leq 1}(l)) \quad (1)$$

Then $N_{crit}(l)$ is the maximum diversity of templates beyond which it becomes likely that at least 1 pair of UID sequences will be within 1 bp of one another.

Figure 7A:
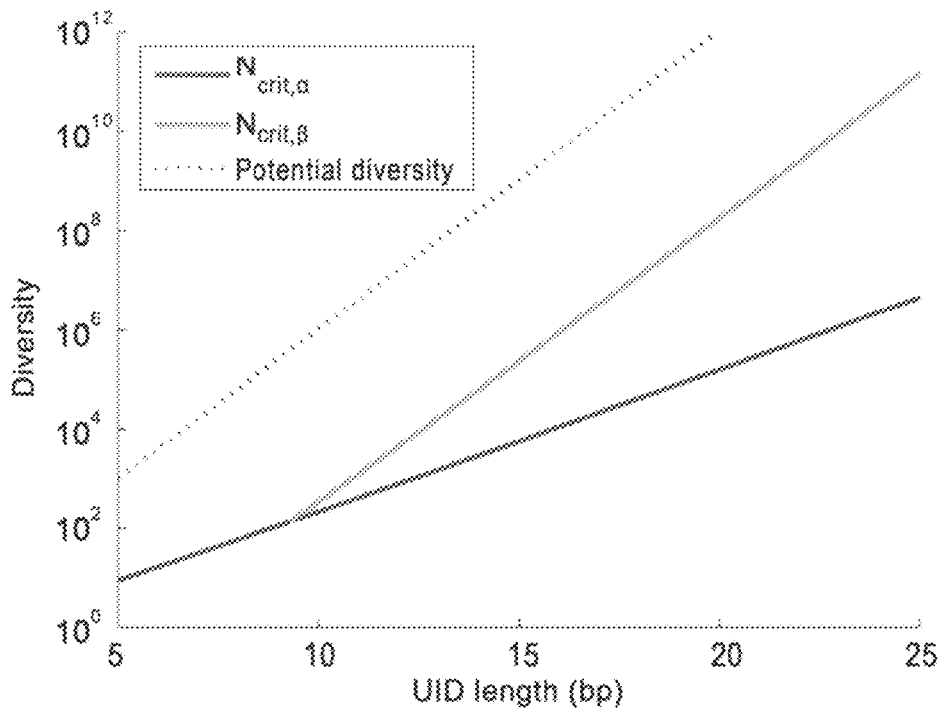
FIG. 7A-B plots the dependences of UID diversity-capacity (the maximum number of unique UID's that can co-exist within a data-set beyond which they begin to become indistinguishable) on UID length and target-sequence diversity. α-UID's must in general rely entirely on their own sequences to be distinguishable, and therefore their diversity-capacity $N_{crit,α}(l)$, a simple evaluation of equation (1), is plotted in FIG. 7A. β-UID's may be distinguished in the same manner (and therefore their diversity-capacity will not be any lower than an α-UID of the same length), however if two indistinguishable β-UID's correspond to two distinguishable pairs of α-UID's, such a β-UID can be discarded. The point at which this requires discarding significant data is the evaluation of equation (2), and is plotted as $N_{crit,β}(l)$ in FIG. 7A. The effect of target-sequence diversity, quantified by the Simpson Index, on α-UID diversity-capacity is plotted in FIG. 7B.
Figure 7B:
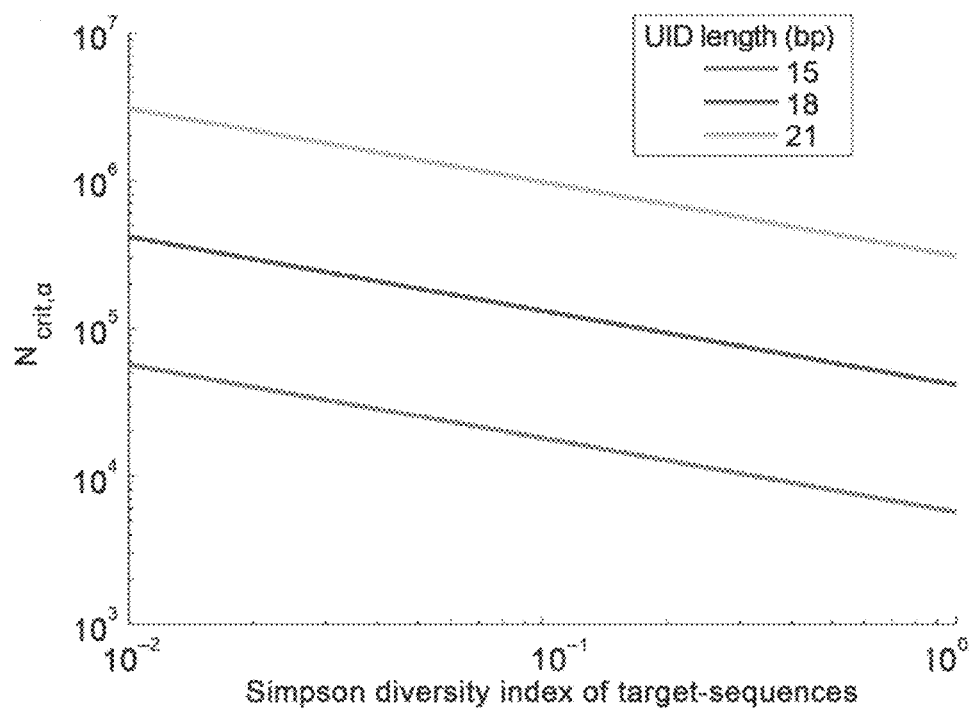

This straightforward definition of distinguishability is relevant in general, if the UID-sequence is the sole criterion for determining identity (see blue line in FIG. 7A). Meanwhile, distinguishability of UID's, and α-UID's in particular, may be augmented by exploiting the diversity of DNA-sequence targets they label. For a set of sequence frequencies $\{p_1, p_2, \ldots, p_s\}$ (normalized to sum to one) of S distinct target sequence-types, the probability that two randomly selected α-UID-labeled targets will have the same sequence-type is $\lambda=\Sigma_i p_i^2$. This measure, also known as Simpson's diversity index, affects the calculation above by multiplying $P_{\leq 1}$, to generate an effective probability equal to that of two α-UID's are mutually indistinguishable and label sequence-types that are also indistinguishable. The more diverse and distributed the population of sequences, the smaller the product $\lambda P_{\leq 1}$ and the larger the value of $N_{crit}(l)$. The effect of changing the diversity index on the value of $N_{crit}$, for different values of (l) is depicted in FIG. 7B.

β-UID's allow for greater diversity than α-UID's of the same length for the reason that no substantial cost may be incurred from discarding β-UID found to link more than two α-UID's. Applicants may therefore define a new critical diversity (of β-UID-labeled cross-linking events this time), $N_{crit,\beta}(l)$ that Applicants define as the diversity of β-UID-labeled cross-linking events beyond which more than 1% must be discarded due to the existence of more than two α-UID-pairs associating with them (FIG. 7A):

$$0.01 \times N_{crit,\beta}(l) = (1-(1-P_{\leq 1})^{N_{crit,\beta}(l)-1}) \times N_{crit,\beta}(l) \quad (2)$$

β-UID delivery by overlap-extension PCR involves diffusion between stochastically distributed α-UID-tagged molecules. Molecular microscopy or VIPUR microscopy seeks to use resulting α- and β-UID associations to infer sequence-location. Therefore, analysis of PCR reaction-diffusion dynamics can yield insight into both spatial resolution and the experimental variables affecting it. Consider the diffusion profile of products of an α-UID with index i, centered at position $x_i$.

$$c_i(\vec{x}) \propto t^{-d/2} e^{-\|\vec{x}-\vec{x}_i\|^2/4dDt + At} \quad (3)$$

where d is the dimensionality (of space), D is the diffusion constant, and A=(log 2)/Δt where Δt is the time-scale of a PCR cycle. The rate of cross-link product (ie new β-UID) formation between α-UID's i and j is then the volume-integral $$r_{ij}(t) \propto \int_{\vec{x}} c_i(\vec{x}_i, \vec{x}, t) c_j(\vec{x}_j, \vec{x}, t) dV \quad (4)$$

$$\propto t^{-d} e^{-\|\vec{x}_i - \vec{x}_j\|^2 / 8dDt + 2At} \int_{\vec{x}} e^{-\|x - (\vec{x}_i + \vec{x}_j)/2\|^2 / 2dDt} dV$$

$$\propto t^{-d/2} e^{-\|\vec{x}_i - \vec{x}_j\|^2 / 8dDt + 2At}$$

where in the above, consider events generated at rate $r_{ij}(t)$ to be distinct from events generated by $r_{ij}(t)$ (for tracking the exact sequence-form of the dimer). The expected number of cross-link events between UID i and any other UID j at any given time $t \geq \tau_{min}$ for an average template concentration $\rho$ is then $$\int_V r_{ij}(t) \propto \begin{cases} t^{-d/2} e^{2At}, & j = i \\ t^{-d/2} e^{2At} \int_V dV \frac{\rho}{N} e^{-\|\vec{x}\|^2/8dDt} = \\ e^{2At} \frac{\rho}{N} (8\pi dD)^{d/2}, & j \neq i \end{cases} \quad (5)$$

where N is the total number of α-UID's from which the total density $\rho$ originates. In Target-Target Molecular Microscopy, in which self-to-self dimerization is allowed, after time τ, the fraction of the total of new cross-linking events that are self-to-self is $$s(\tau) = \frac{r_{ii}(\tau) + r_{jj}(\tau) + \cdots}{r_{ii}(\tau) + r_{ij}(\tau) + \cdots + r_{jj}(\tau) + r_{ji}(\tau) + \cdots}$$

$$= \frac{1}{1 + \rho(8\pi dD\tau)^{d/2}}$$

The fraction abundance of self-to-self dimers after termination time T, $\alpha(T)$, may be calculated by convolving diversity generated at time τ into expected resultant abundance after time T, $e^{A(T-\tau)}$.

This gives $$a(T) = \frac{\int_{\tau_{min}}^T \tau^{-d/2} e^{2A\tau} e^{A(t-\tau)} d\tau}{\int_{\tau_{min}}^T e^{2A\tau} e^{A(T-\tau)} (\tau^{-d/2} + \rho(8\pi dD)^{d/2}) d\tau}$$

$$= \left(1 + \frac{\int_{\tau_{min}}^T \rho e^{A\tau} (8\pi dD)^{d/2} d\tau}{\int_{\tau_{min}}^T e^{A\tau} \tau^{-d/2} d\tau}\right)^{-1}$$

$$= \left(1 + \frac{\rho(e^{AT} - e^{A\tau_{min}})(8\pi dD)^{d/2}}{A \int_{\tau_{min}}^T e^{A\tau} \tau^{-d/2} d\tau}\right)^{-1}$$

Here, $\tau_{min}$ is the time when cross-linking selectively begins (not 0), only after which different β-UID's compete for predominance.

The above expressions for $s(\tau)$ and $a(T)$ designate the required sensitivity of an experiment seeking to resolve the spatial location of an α-UID-tagged sequence relative to neighboring sequences distributed with average density $\rho$. Above the maximum density $\rho$ determined by the minimum values of $s(\tau)$ and $a(T)$ detectable by a given sequencing-depth, self-to-self dimer products will occur at frequencies comparable to self-to-nonself dimers, making the corresponding α-UID locations indistinguishable from one another.

The abundance or representation of cross-linking events within the data-set should go as follows. Letting the rate of generation of new individual β-UID's be $e^{2At}$, Applicants get the probability of a randomly-sampled β-UID having been generated at time τ

$$\text{Prob}(\tau) \propto e^{-2A\tau} dt$$

Meanwhile, final β-UID abundance $n = e^{A(T-\tau)}$ and therefore $dn/n = -Ad\tau$. Therefore $\text{Prob}(n) \propto n^{-3} dn$.

From equation (5), $r_{tot}(\tau) = \alpha e^{2A\tau}(\tau^{-d/2} + \rho(8\pi dD)^{d/2})$ where α is a constant that brings $r(\tau)$ into units of events-per-unit-time. This allows the rank-order event-times (for the kth earliest cross-linking event) to be written as $\{\tau_k\}$ as $$\int_{\tau_k}^{\tau_{k+1}} r_{tot}(\tau) d\tau = 1$$

where to $\tau_0 = 0$. Realistically, cross-linking will only become frequent after a few cycles and therefore $r_{tot}(\tau) \approx e^{A(2\tau)} \alpha \rho (8\pi dD)^{d/2}$ is expected. This then gives $$\tau_k = \frac{1}{2A} \log(1 + 2kA/\alpha')$$

where $\alpha' = \alpha \rho (8\pi dD)^{d/2}$. Because the abundance of a β-UID generated at $\tau_\kappa$ is $n(\tau_\kappa) \approx e^{A(T-\tau_k)}$ when the experiment terminates at time T, the abundance of the kth most abundant β-UID is $$n_k = n(\tau_k) = e^{AT}\left(1 + \frac{2kA}{\alpha'}\right)^{-1/2}$$

$\alpha \ll A$ is expected because it is equivalent to the contribution of cross-linking events between non-same α-UID's to the total cross-linking rate (as seen from the above expression for $r_{tot}(\tau)$) at time 0. Therefore $n_k \sim k^{-1/2}$.

Figure 6:
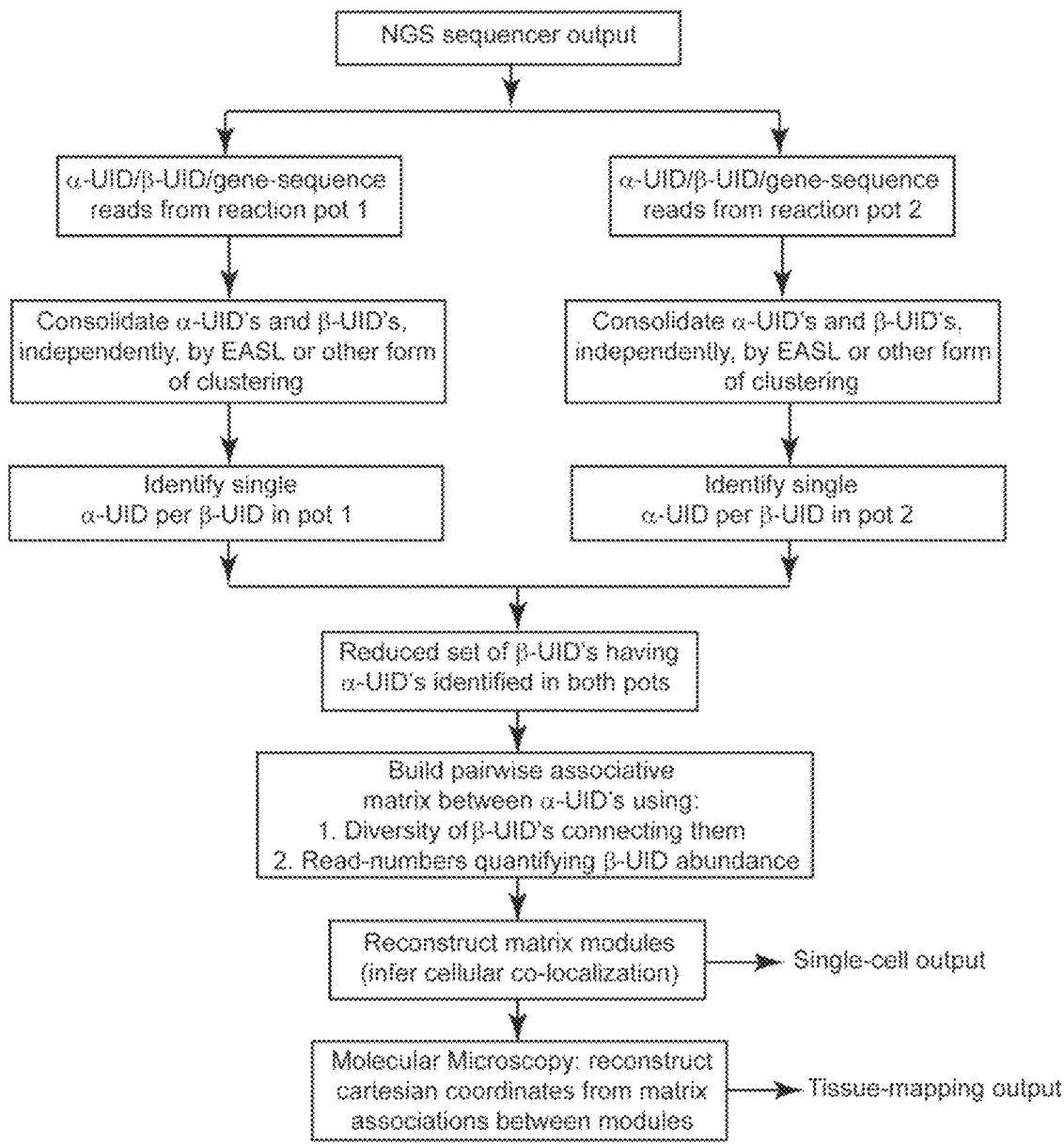
FIG. 6 illustrates the data-flow from Next Generation Sequence output for Target-Target Molecular Microscopy.
Figure 8:
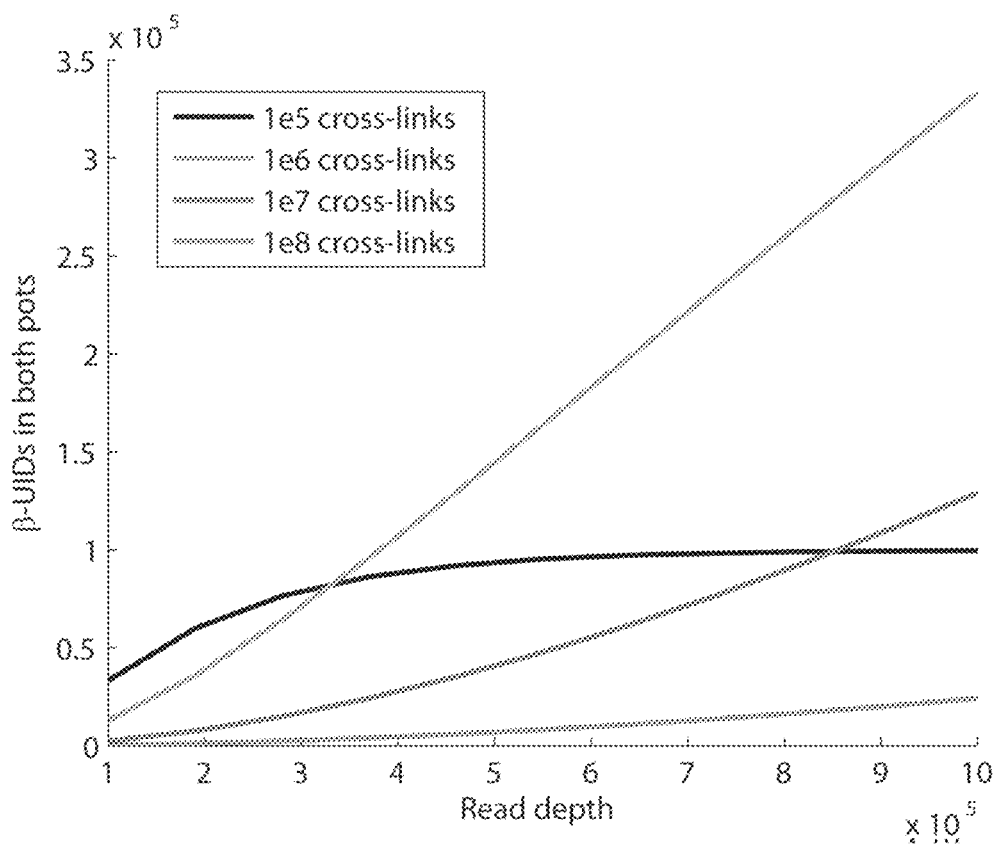
FIG. 8 depicts capture of β-UID's from Target-Target Molecular Microscopy in 2 reaction pots as a function of read-depth R (with R reads sequenced in both pots) and total β-UID diversity (the latter represented by different colors).
Figure 9A:
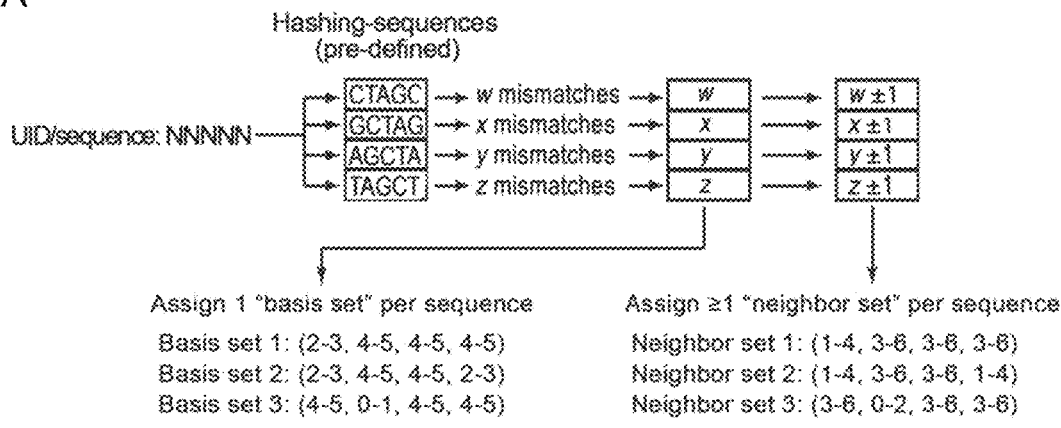
FIG. 9A-B illustrates fast pairwise alignments of UID's sequenced by NGS. (A) In the example depicted, a sequenced 5 bp UID is compared to 4 hashing-sequences of equal length. Based on the number of mismatches relative to each of these hashing-sequences, the UID is assigned to a single "basis set" and one or more "neighbor sets" consisting of only those sequences whose mismatch profiles are consistent with being 1 bp different from a member of their corresponding neighbor sets (B). A full pairwise comparison of N different UID sequences would require N(N−1)/2 alignments, or 6 alignments for 4 UID's. However, partitioning 4 distinct UID's in the illustrated example into basis- and neighbor-sets allows the number of alignments to be reduced to 2.
Figure 9B:
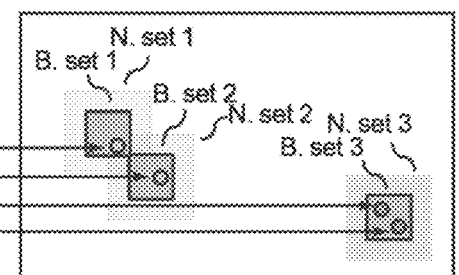
Figure 9B:
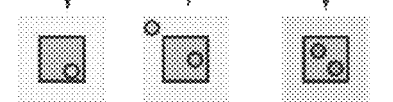

Target-Target Molecular Microscopy, with experimental and computational workflows illustrated in FIG. 3 and FIG. 6, respectively, require a particular β-UID to be re-captured in two reaction pots. In order to determine the frequency at which this happens as well as the read-depth required to achieve recapture, Applicants use the abundance-distribution above. The number of events φ found in two reactions each sampled R times from the pool of post-reaction products that are independently sampled from the ensemble is $$\phi = \sum_{k=1}^{k_{max}} \left(1 - \left(1 - \frac{k^{-1/2}}{\sum_{k'} k'^{-1/2}}\right)^R\right)\left(1 - \left(1 - \frac{k^{-1/2}}{\sum_{k'} k'^{-1/2}}\right)^R\right)$$

where $k_{max}$ is the total β-UID diversity being sampled from. This dependence of observed β-UID abundance on total β-UID diversity and sequencing depth is illustrated in FIG. 8. It is important to note that this recapture estimate reflects perfect sample recovery from the after in situ amplification in the Target-Target Molecular Microscopy workflow (FIG. 3).

Optimizing primer concentration during overlap-extension PCR is essential for finding a balance between amplification of monomeric products with these primers and the competing cross-annealment of these monomeric products to each other.

Applicants may analyze the effect of increasing or decreasing primer-concentration during overlap-extension PCR with the following calculation. Returning to the amplifying diffusion profile $c_i(\vec{x}_i, \vec{x}, t)$ of an α-UID with index i, centered at position $\vec{x}_i$ in equation (3), the cross-link formation rate $r_{ij}(t)$ may be made more exact by noting its dependence on primer concentration p. Primers will compete directly with potential cross-link partners. Now for $p \gg \Sigma_i c_i(\vec{x}_i, \vec{x}, t)$ for all $\vec{x}$, $r_{ij}(t)$ may be written $$r_{ij}(p, t) \propto \int_{\vec{x}} c_i(\vec{x}_i, \vec{x}, t) \left( \frac{c_j(\vec{x}_j, \vec{x}, t)}{\sum_j c_j(\vec{x}_j, \vec{x}, t) + p} \right) dV$$

$$\propto t^{-d/2} e^{-\|\vec{x}_i - \vec{x}_j\|^2 / 8dDt + 2A(p)t}.$$

$$\frac{1}{p}\left(1 + O\left(\frac{\sum_j c_j(\vec{x}_j, \vec{x}, t)}{p}\right)\right)$$

where A(p) denotes the primer-concentration-dependent amplification rate. The primer dependence of the cross-linking rate is therefore a delicate balance between the terms $e^{2A(p)t}$ and p.

The function A(p) may be viewed as expressing the probability that during a given cycle a primer will anneal to a given template. If the primer concentration is infinite (barring extreme physical consequences of this) this probability is 1, and as before $A(p) = \log 2/\Delta t$. Meanwhile, for annealing time $\tau_a$ and annealing rate-per-unit-concentration $k_a$, $A(p) = \log(2 - e^{-k_a p \tau_a})/\Delta t$. As before, assume primer-concentration far exceeds the concentration of cross-link products with which it might potentially compete for annealing sites, in addition to the reaction being far from primer-depletion.

Therefore, if $$\frac{\partial}{\partial p}\left[\exp\left(2t\log\left(2 - e^{-\tilde{k}_a p \tau_a}\right)/\Delta t\right)^*/p\right] > 0,$$

higher primer concentrations will increase overall cross-linking rates, and otherwise they will decrease cross-linking rates. Evaluating and rewriting this criterion $$\frac{2k_a \tau_a C p}{2 e^{k_a \tau_a p} - 1} > 1 \quad (5)$$

where C is the total number of cycles up to this point in the experiment.

The value of $k_a \tau_a p$ can be calculated indirectly by looking at the degree to which a change in primer concentration leads to a change in the abundance of PCR product. If an N-fold change in PCR product is observed due to an M-fold change in primer concentration, then $$N(2 - e^{-k_a p \tau_a})^C = (2 - e^{-M k_a p \tau_a})^C$$

From this, the value of $k_a \tau_a p$ may be found and the discriminant from equation (5) may be evaluated.

A diffusion constant for a linear 5.9 kb construct at D=1.28 μm²/s at T=297K with a scaling relationship D~$L^{-0.571 \pm 0.014}$, giving a diffusion constant for linearized 300 bp DNA at 7 μm²/s was previous reported (Robertson et al., Diffusion of isolated DNA molecules: Dependence on length and topology. Proc Natl Acad Sci USA. May 9, 2006: 103(19): 7310-7314). Temperature dependence will make the diffusion coefficient vary as ~T/η(T), where η(T) is the temperature-dependent viscosity of the solution. The viscosity of water as a ratio to viscosity at temperature at 293K is ~0.5 at 60° C., ~0.4 at 75° C., and ~0.3 at 95° C. Taking ~0.4 as reflective of the average, the following is expected $$T_{75° C.}/\eta(T_{75° C.}) \approx 3 \times T_{25° C.}/\eta(T_{75° C.})$$

Therefore, the diffusion constant for a 300 bp amplicon during PCR may be estimated, in free solution, at ~21 μm²/s.

In an example of a free-solution experiment, one starts out with 100 ng/μl total RNA, or, assuming 20 pg per cell, 5000 cells/μl. If up to 1000 fluorescent-protein transcripts are allowed per cell, this gives $5 \times 10^6$ transcripts per μl. After dilution within the experiment (1:11 during RT, 2.3:13.3 during exonuclease-I treatment, 4:25 during 2nd strand synthesis, and finally 1:12.5 for overlap-extension PCR), this is cut to $10^3$ transcripts per μl, or $10^{-6}$/μm³. In units of μm and s, plugging ρ=$10^{-6}$, d=3, and D=21 into the expression for s(τ), for τ=1000s, one gets s(τ)≈$5 \times 10^{-4}$ for the fraction of events occurring at τ=1000s to be self-to-self.

Figure 10B:
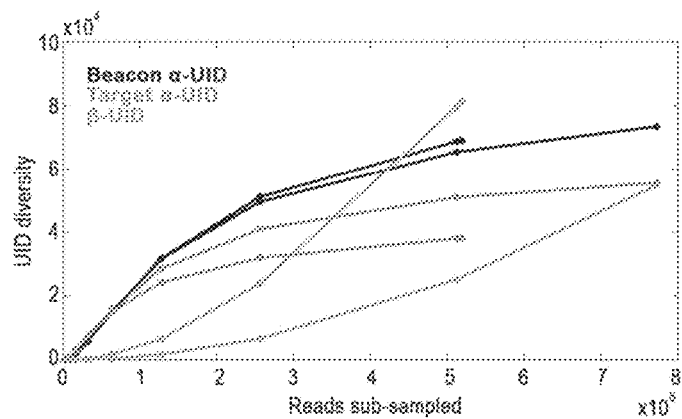

Analysis of the saturation of the algorithm upon deep sequencing, with cluster-sizes required to include at least 2 reads, can be found in the rarefaction plot in FIG. 10B. Data is taken from a Beacon-Target Molecular Microscopy experiment where in situ PCR is performed in a PEG hydrogel.

Figure 5:
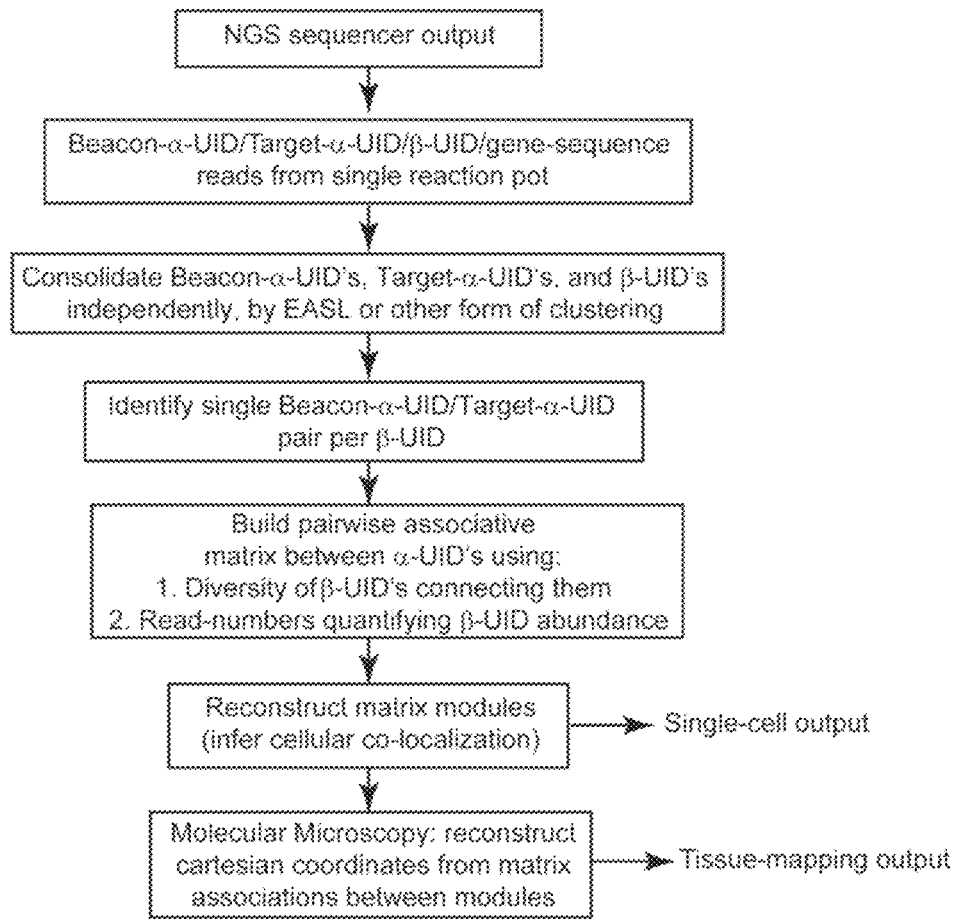
FIG. 5 illustrates the data-flow from Next Generation Sequence output for Beacon-Target Molecular Microscopy.

Final data-processing is performed as illustrated in flow-charts in FIG. 5, for Beacon-Target Molecular Microscopy, and FIG. 6, for Target-Target Molecular Microscopy.

In Target-Target Molecular Microscopy (FIG. 6), the sequence read-out is partitioned according to which amplicon it corresponds to. α-UID's and β-UID's are identified and clustered independently. Subsequently, based on read-abundance, a single α-UID is identified per β-UID in each pool of amplicons. β-UID's in the two amplicon pools are then compared, and those found in both have their α-UID's paired. For each pair of α-UID's, pairwise association is calculated using the diversity of unique β-UID's to which the pair corresponds and/or the abundance of these β-UID's, quantified by read-count. Based on the similarity of associations of α-UID-labeled targets, and equation (4), pairwise distances are inferred. These are then used to deduce cellular co-localization, as well as the physical adjacency and therefore relative locations of cells, In Beacon-Target Molecular Microscopy (FIG. 5), the sequence read-out is taken from a single amplicon comprising a beacon α-UID, a target α-UID and a β-UID. After being identified across the data-set, these are each clustered independently. Subsequently, based on read-abundance, a single beacon/target α-UID pair is identified per β-UID. An association matrix between beacons and targets is formed from this data directly, using the diversity of unique β-UID's to which the pair corresponds and/or the abundance of these β-UID's, quantified by read-count.

Fixation of cells or tissue may involve the use of cross-linking agents, such as formaldehyde, and may involve embedding cells or tissue in a paraffin wax or polyacrylamide support matrix (Chung K, et al. Nature. 2013 May 16; 497(7449): 322-7).

Amplification may involve thermocycling or isothermal amplification (such as through the methods RPA or LAMP). Cross-linking may involve overlap-extension PCR (the current method, illustrated in attached figures) or use of ligase or capture beads to associate multiple amplification products with each other.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of *E. coli* DNA polymerase, and reverse transcriptase. A preferred amplification method is PCR. In particular, the isolated RNA can be subjected to a reverse transcription assay that is coupled with a quantitative polymerase chain reaction (RT-PCR) in order to quantify the expression level of a sequence associated with a signaling biochemical pathway.

Detection of the gene expression level can be conducted in real time in an amplification assay. In one aspect, the amplified products can be directly visualized with fluorescent DNA-binding agents including but not limited to DNA intercalators and DNA groove binders. Because the amount of the intercalators incorporated into the double-stranded DNA molecules is typically proportional to the amount of the amplified DNA products, one can conveniently determine the amount of the amplified products by quantifying the fluorescence of the intercalated dye using conventional optical systems in the art. DNA-binding dye suitable for this application include SYBR green, SYBR blue, DAPI, propidium iodine, Hoeste, SYBR gold, ethidium bromide, acridines, proflavine, acridine orange, acriflavine, fluorocoumanin, ellipticine, daunomyc in, chloroquine, distamyc in D, chromomyc in, homidium, mithramycin, ruthenium polypyridyls, anthramycin, and the like.

In another aspect, other fluorescent labels such as sequence specific probes can be employed in the amplification reaction to facilitate the detection and quantification of the amplified products. Probe-based quantitative amplification relies on the sequence-specific detection of a desired amplified product. It utilizes fluorescent, target-specific probes (e.g., TaqMan® probes) resulting in increased specificity and sensitivity. Methods for performing probe-based quantitative amplification are well established in the art and are taught in U.S. Pat. No. 5,210,015.

Sequencing may be performed on any high-throughput platform with read-length (either single- or paired-end) sufficient to cover both template and cross-linking event UID's. Methods of sequencing oligonucleotides and nucleic acids are well known in the art (see, e.g., WO93/23564, WO98/28440 and WO98/13523; U.S. Pat. Nos. 5,525,464; 5,202,231; 5,695,940; 4,971,903; 5,902,723; 5,795,782; 5,547,839 and 5,403,708; Sanger et al., Proc. Natl. Acad. Sci. USA 74:5463 (1977); Drmanac et al., Genomics 4:114 (1989); Koster et al., Nature Biotechnology 14:1123 (1996); Hyman, Anal. Biochem. 174:423 (1988); Rosenthal, International Patent Application Publication 761107 (1989); Metzker et al., Nucl. Acids Res. 22:4259 (1994); Jones, Biotechniques 22:938 (1997); Ronaghi et al., Anal. Biochem. 242:84 (1996); Ronaghi et al., Science 281:363 (1998); Nyren et al., Anal. Biochem. 151:504 (1985); Canard and Arzumanov, Gene 11:1 (1994); Dyatkina and Arzumanov, Nucleic Acids Symp Ser 18:117 (1987); Johnson et al., Anal. Biochem. 136:192 (1984); and Elgen and Rigler, Proc. Natl. Acad. Sci. USA 91(13):5740 (1994), all of which are expressly incorporated by reference).

The present invention may be applied to (1) single-cell transcriptomics: cDNA synthesized from mRNA is barcoded and cross-linked during in situ amplification, (2) single-cell proteomics: cDNA or DNA synthesized from RNA- or DNA-tagged antibodies of one or multiple specificities maps the abundance and distributions of different protein-antigens and (3) whole-tissue transcriptomic/proteomic mapping (molecular microscopy or VIPUR microscopy): using the frequency of cross-contamination between cells to determine their physical proximity, and via applications (1) single-cell transcriptomics and (2) single-cell proteomics, determining the global spatial distribution of mRNA, protein, or other biomolecules in a biological sample. This may be used, for example, to screen for anti-cancer/pathogen immunoglobulins (by analyzing co-localization of B-cells and T-cells within affected tissue) for immunotherapy.

TABLE 1

Techniques for overlap-extension suppression during library preparation.

| Technique | Description |
|---|---|
| Blocking oligos | 3'-capped oligos complementary to both overlap-extension ends (10 and 10' in FIG. 2) added at high concentration during NGS library preparation phase (FIG. 2, vi). See Turchaninova MA et al. Eur J Immunol. 2013 Sep; 43(9): 2507-15. |
| T7-exo + Exo-I treatment | At least 3 phosphorothioate nucleotides are added to each 5' end of primers (5) and (8) for use during in situ amplification. After elution, products are digested with both T7-exonuclease and exonuclease I in order to eliminate monomeric products. |
| Biotin pulldown | Biotin is added to either primer (5) or primer (8) for use during in situ amplification. After elution, products are pulled down with streptavidin beads, in order eliminate either one of the monomeric products. |

TABLE 2

List of primer-sequences for Beacon-Target β-UID delivery.

| Stage used | Alias | Sequence | SEQ ID NO: |
|---|---|---|---|
| Reverse transcription | (5)-(2)-(4)-GAPDH | GACGTGTGCTCTTCCGATCTTNNNNNNN-NATNNNN NNNATNNNNNNNNTTACTCCTTGGAGGCCATGT | 1 |
| Reverse transcription | (5)-(2)-(4)-GFP | GACGTGTGCTCTTCCGATCTTNNNNNNN-NATNNNN NNNATNNNNNNNNTCTTGAAGTTCACCTTGATGC | 2 |
| Reverse transcription | (5)-(2)-(4)-mCh | GACGTGTGCTCTTCCGATCTTNNNNNNN-NATNNNN NNNATNNNNNNNNCCATGGTCTTCTTCTGCATT | 3 |

TABLE 2-continued

List of primer-sequences for Beacon-Target β-UID delivery.

| Stage used | Alias | Sequence | SEQ ID NO: |
|---|---|---|---|
| Reverse transcription | (3)-(2)-(1)-ACTB | TTGAGGTGTCCTAAACTTACGCNNNNNN-NATNNN NNNNATNNNNNNNCTAGAGAAGTGGGGTG-GCTTT T | 4 |
| 2nd strand-synthesis/ linear amp | (9sh)-(7(-))-GAPDH | TGGTCTCAACATATCGCATCCTGGGCTA-CACTGA GCACCAGG | 5 |
| 2nd strand-synthesis/ linear amp | (9sh)-(7(-))-GFP | TGGTCTCAACATATCGCACCATCTTCT-TCAAGGA CGACGGCAAC | 6 |
| 2nd strand-synthesis/ linear amp | (9sh)-(7(-))-mCh | TGGTCTCAACATATCGCAGTTCATGTACG-GCTCC AAGGCCTAC | 7 |
| 2nd strand-synthesis/ linear amp | (8sh)-(6(-))-ACTB | TGGCTTCAAATTCACGCAAACTGGAACGGT-GAAG GTGACAGCAG | 8 |
| OE-PCR | (5) | GTTCAGACGTGTGCTCTTCCGATCT | 9 |
| OE-PCR | (8) | ATGAGTGGCTTCAAATTCACGC | 10 |
| OE-PCR | (10')-(2)-(9) | TATTCCCATGGCGCGCCANNNNNATNNNNNT-TGA GGTGTCCTAAACTTACGC | 11 |
| OE-PCR | (10)-(2)-(3) | GGCGCGCCATGGGAATAANNNN-NATNNNNNTGGA GTGGTCTCAACATATCGC | 12 |
| Re-amplification/ library prep | (1'(long)) | CCCTACACGACGCTCTTCCGATCTCTCCATC-CTA AAAGCCACCCCACTTCTCTA | 13 |
| Re-amplification/ library prep | (12)-(5) | CAAGCAGAAGACGGCATACGAGATATTC-CTCTGT GACTGGAGTTCAGACGTGTGCTCTTCCGATCT | 14 |

The number of random nucleotides in primers beginning with are determined by either the expected diversity of template cDNA molecules being amplified (for α-UID diversity, in the case of (5)-(2)-X and (3)-(2)-X) or the expected diversity required to uniquely identify overlap-extension events (for β-UID diversity, in the case of (10)-(2)-X and (10')-(2)-X).
The terms "polynucleotide", "nucleotide", "nucleotide sequence", "nucleic acid" and "olignucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein the term "wild type" is a term of the art understood by skilled persons and means the typical form of an organism, strain, gene or characteristic as it occurs in nature as distinguished from mutant or variant forms.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences.

Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. % homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p387). Examples of other software than may perform sequence comparisons include, but are not limited to, the BLAST package (see Ausubel et al., 1999 Short Protocols in Molecular Biology, 4th Ed.—Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999 174(2): 247-50; FEMS Microbiol Lett. 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result.

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Hybridization can be performed under conditions of various stringency. Suitable hybridization conditions for the practice of the present invention are such that the recognition interaction between the probe and sequences associated with a signaling biochemical pathway is both sufficiently specific and sufficiently stable. Conditions that increase the stringency of a hybridization reaction are widely known and published in the art. See, for example, (Sambrook, et al., (1989); Nonradioactive In Situ Hybridization Application Manual, Boehringer Mannheim, second edition). The hybridization assay can be formed using probes immobilized on any solid support, including but are not limited to nitrocellulose, glass, silicon, and a variety of gene arrays. A preferred hybridization assay is conducted on high-density gene chips as described in U.S. Pat. No. 5,445,934.

For a convenient detection of the probe-target complexes formed during the hybridization assay, the nucleotide probes are conjugated to a detectable label. Detectable labels suitable for use in the present invention include any composition detectable by photochemical, biochemical, spectroscopic, immunochemical, electrical, optical or chemical means. A wide variety of appropriate detectable labels are known in the art, which include fluorescent or chemiluminescent labels, radioactive isotope labels, enzymatic or other ligands. In preferred embodiments, one will likely desire to employ a fluorescent label or an enzyme tag, such as digoxigenin, β-galactosidase, urease, alkaline phosphatase or peroxidase, avidin/biotin complex.

The detection methods used to detect or quantify the hybridization intensity will typically depend upon the label selected above. For example, radiolabels may be detected using photographic film or a phosphoimager. Fluorescent markers may be detected and quantified using a photodetector to detect emitted light. Enzymatic labels are typically detected by providing the enzyme with a substrate and measuring the reaction product produced by the action of the enzyme on the substrate; and finally colorimetric labels are detected by simply visualizing the colored label.

Examples of the labeling substance which may be employed include labeling substances known to those skilled in the art, such as fluorescent dyes, enzymes, coenzymes, chemiluminescent substances, and radioactive substances. Specific examples include radioisotopes (e.g., $^{32}$P, $^{14}$C, $^{125}$I, $^{3}$H, and $^{131}$I), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

Advantageously, the label is a fluorescent label. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine The fluorescent label may be a fluorescent protein, such as blue fluorescent protein, cyan fluorescent protein, green fluorescent protein, red fluorescent protein, yellow fluorescent protein or any photoconvertible protein. Colormetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terrylen. In the alternative, the fluorescent label may be a fluorescent bar code.

In an advantageous embodiment, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation.

In an advantageous embodiment, agents may be uniquely labeled in a dynamic manner (see, e.g., international patent application serial no. PCT/US2013/61182 filed Sep. 23, 2012). The unique labels are, at least in part, nucleic acid in nature, and may be generated by sequentially attaching two or more detectable oligonucleotide tags to each other and each unique label may be associated with a separate agent. A detectable oligonucleotide tag may be an oligonucleotide that may be detected by sequencing of its nucleotide sequence and/or by detecting non-nucleic acid detectable moieties to which it may be attached.

The oligonucleotide tags may be detectable by virtue of their nucleotide sequence, or by virtue of a non-nucleic acid detectable moiety that is attached to the oligonucleotide such as but not limited to a fluorophore, or by virtue of a combination of their nucleotide sequence and the nonnucleic acid detectable moiety.

In some embodiments, a detectable oligonucleotide tag may comprise one or more nonoligonucleotide detectable moieties. Examples of detectable moieties may include, but are not limited to, fluorophores, microparticles including quantum dots (Empodocles, et al., Nature 399:126-130, 1999), gold nanoparticles (Reichert et al., Anal. Chem. 72:6025-6029, 2000), microbeads (Lacoste et al., Proc. Natl. Acad. Sci. USA 97(17):9461-9466, 2000), biotin, DNP (dinitrophenyl), fucose, digoxigenin, haptens, and other detectable moieties known to those skilled in the art. In some embodiments, the detectable moieties may be quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique label may be produced by sequentially attaching two or more detectable oligonucleotide tags to each other. The detectable tags may be present or provided in a plurality of detectable tags. The same or a different plurality of tags may be used as the source of each detectable tag may be part of a unique label. In other words, a plurality of tags may be subdivided into subsets and single subsets may be used as the source for each tag.

In some embodiments, a detectable oligonucleotide tag comprises one or more non-oligonucleotide detectable moieties. Examples of detectable moieties include, but are not limited to, fluorophores, microparticles including quantum dots (Empodocles, et al., Nature 399:126-130, 1999), gold nanoparticles (Reichert et al., Anal. Chem. 72:6025-6029, 2000), microbeads (Lacoste et al., Proc. Natl. Acad. Sci. USA 97(17):9461-9466, 2000), biotin, DNP (dinitrophenyl), fucose, digoxigenin, haptens, and other detectable moieties known to those skilled in the art. In some embodiments, the detectable moieties are quantum dots. Methods for detecting such moieties are described herein and/or are known in the art.

Thus, detectable oligonucleotide tags may be, but are not limited to, oligonucleotides comprising unique nucleotide sequences, oligonucleotides comprising detectable moieties, and oligonucleotides comprising both unique nucleotide sequences and detectable moieties.

A unique nucleotide sequence may be a nucleotide sequence that is different (and thus distinguishable) from the sequence of each detectable oligonucleotide tag in a plurality of detectable oligonucleotide tags. A unique nucleotide sequence may also be a nucleotide sequence that is different (and thus distinguishable) from the sequence of each detectable oligonucleotide tag in a first plurality of detectable oligonucleotide tags but identical to the sequence of at least one detectable oligonucleotide tag in a second plurality of detectable oligonucleotide tags. A unique sequence may differ from other sequences by multiple bases (or base pairs). The multiple bases may be contiguous or non-contiguous. Methods for obtaining nucleotide sequences (e.g., sequencing methods) are described herein and/or are known in the art.

In some embodiments, detectable oligonucleotide tags comprise one or more of a ligation sequence, a priming sequence, a capture sequence, and a unique sequence (optionally referred to herein as an index sequence). A ligation sequence is a sequence complementary to a second nucleotide sequence which allows for ligation of the detectable oligonucleotide tag to another entity comprising the second nucleotide sequence, e.g., another detectable oligonucleotide tag or an oligonucleotide adapter. A priming sequence is a sequence complementary to a primer, e.g., an oligonucleotide primer used for an amplification reaction such as but not limited to PCR. A capture sequence is a sequence capable of being bound by a capture entity. A capture entity may be an oligonucleotide comprising a nucleotide sequence complementary to a capture sequence, e.g. a second detectable oligonucleotide tag or an oligonucleotide attached to a bead. A capture entity may also be any other entity capable of binding to the capture sequence, e.g. an antibody or peptide. An index sequence is a sequence comprising a unique nucleotide sequence and/or a detectable moiety as described above.

"Complementary" is a term which is used to indicate a sufficient degree of complementarity between two nucleotide sequences such that stable and specific binding occurs between one and preferably more bases (or nucleotides, as the terms are used interchangeably herein) of the two sequences. For example, if a nucleotide in a first nucleotide sequence is capable of hydrogen bonding with a nucleotide in second nucleotide sequence, then the bases are considered to be complementary to each other. Complete (i.e., 100%) complementarity between a first nucleotide sequence and a second nucleotide is preferable, but not required for ligation, priming, or capture sequences.

The present invention also relates to a computer system involved in carrying out the methods of the invention relating to both computations and sequencing.

A computer system (or digital device) may be used to receive, transmit, display and/or store results, analyze the results, and/or produce a report of the results and analysis. A computer system may be understood as a logical apparatus that can read instructions from media (e.g. software) and/or network port (e.g. from the internet), which can optionally be connected to a server having fixed media. A computer system may comprise one or more of a CPU, disk drives, input devices such as keyboard and/or mouse, and a display (e.g. a monitor). Data communication, such as transmission of instructions or reports, can be achieved through a communication medium to a server at a local or a remote location. The communication medium can include any means of transmitting and/or receiving data. For example, the communication medium can be a network connection, a wireless connection, or an internet connection. Such a connection can provide for communication over the World Wide Web. It is envisioned that data relating to the present invention can be transmitted over such networks or connections (or any other suitable means for transmitting information, including but not limited to mailing a physical report, such as a print-out) for reception and/or for review by a receiver. The receiver can be but is not limited to an individual, or electronic system (e.g. one or more computers, and/or one or more servers).

In some embodiments, the computer system comprises one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other suitable storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

A client-server, relational database architecture can be used in embodiments of the invention. A client-server architecture is a network architecture in which each computer or process on the network is either a client or a server. Server computers are typically powerful computers dedicated to managing disk drives (file servers), printers (print servers), or network traffic (network servers). Client computers include PCs (personal computers) or workstations on which users run applications, as well as example output devices as disclosed herein. Client computers rely on server computers for resources, such as files, devices, and even processing power. In some embodiments of the invention, the server computer handles all of the database functionality. The client computer can have software that handles all the front-end data management and can also receive data input from users.

A machine readable medium comprising computer-executable code may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The subject computer-executable code can be executed on any suitable device comprising a processor, including a server, a PC, or a mobile device such as a smartphone or tablet. Any controller or computer optionally includes a monitor, which can be a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard, mouse, or touch-sensitive screen, optionally provide for input from a user. The computer can include appropriate software for receiving user instructions, either in the form of user input into a set of parameter fields, e.g., in a GUI, or in the form of preprogrammed instructions, e.g., preprogrammed for a variety of different specific operations.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLE

In Situ Chemistry Screening Platform

Glass beads (3 mm, Sigma-Aldrich Z265926) were acid-washed by submersion in 1 M HCl at 55 C for 4-5 hours, with occasional agitation. After being cooled to room temperature, beads were washed 3× in distilled water, followed by washes for 30 min in 50% ethanol, 70% ethanol, and twice in 95% ethanol. All washes were performed while sonicating. Beads were stored sealed in 95% ethanol until further use.

Shortly before experiments, beads were rinsed in acetone, and then treated with 2% APTES (Sigma-Aldrich 440140) in acetone for 60 seconds. Beads were then washed 1× in acetone, followed by 3× in water. Beads were air-dried under a laminar-flow hood, and stored in a sealed container for up to 15 days prior to cell-seeding.

Cell Seeding

Dry beads were removed from sealed container and placed in 25 ul uncured PDMS (with 1:10 dilution of curing agent to PDMS base) in 96 well polypropylene PCR plates. After spinning down at 500×g for 5 min, plates were left to cure overnight at room temperature. After baking 30 min at 80 C, wells were washed with 2× with 70% ethanol, baked again 30 min at 80 C and underwent a final UV-sterilization for 30 minutes in a cell-culture hood. Wells were rinsed with 1×DPBS, and again with DMEM. Wells were then treated with 1:200 dilution of Geltrex (Life Technologies A1413201) in DMEM for 45 minutes at 37 C, and then seeded with suspensions containing 200-250 cells comprising a mixture of HEK-293/GFP (Cell Biolabs AKR-200) and BT-549/RFP (Cell Biolabs AKR-255) cells in volumes of 40 ul of growth medium (10% FBS, 1% NEAA, 1% penicillin-streptomycin in DMEM). Cells were cultured for 36 hours at 37 C.

In Situ Preparation

After culturing, growth medium was removed and cells were washed once with 1×PBS. Cells were fixed in 4% formaldehyde (F8775) in 1×PBS for 15 minutes at room temperature. Formaldehyde was aspirated and replaced by 3×PBS, and left for 10 minutes. Samples were washed twice for 10 minutes in 1×PBS, and then again with water for 1 minute. Samples permeabilized with a solution of 0.25% Triton X-100 (Sigma-Aldrich 93443) in water for 15 minutes, aspirated, and then treated with 0.1 N HCl for 1-5 minutes. After aspiration, samples were washed three times in 1×PBS.

cDNA Preparation

Reverse transcription (RT) was prepared on ice. The RT mix contained 850 nM each of reverse-transcription primers in Table 2 ((5)-(2)-(4)-GAPDH, (5)-(2)-(4)-GFP, (5)-(2)-(4)-mCh, and (3)-(2)-(1)-ACTB), 250 uM of each dNTP species (Enzymatics N2050), 1 U/ul superase-In (Life Technologies AM2696), 4.3 uM DTT, 1×SSIII Buffer (Life Technologies 18080-044), and 10 U/ul SSIII reverse-transcriptase (Life Technologies 18080-044). Samples were treated with RT mix at 60 C for 3 min, followed by 42 C for 1 hour. Afterwards, samples were kept at 4 C for up to 1 hour. Samples were then washed twice with 1×PBS, followed by one wash of water. An exonuclease-I mix was prepared containing 67 mM glycine-KOH, 6.7 mM MgCl$_2$, 10 mM beta-mercaptoethanol, and 1.4 U/ul exonuclease-I (New England Biolabs M0293). Samples were treated with exonuclease-I mix at 37 C for 40 minutes, washed three times in 1×PBS for 1 minute each, and finally washed with water.

In Situ PCR

PCR reactions were prepared in 25 ul as follows. Pre-mixes were prepared containing 2.5 ul 10× HiFi Buffer (Life Technologies 11304-011), 0.2 ul dNTP (25 mM), 0.75 ul MgSO$_4$ (50 mM), 1.6 mg of acrylate-PEG-linker (4arm-PEG-ACRL, MW 10 kDa, Laysan Bio) in 5.25 ul water, and 0.1 ul Platinum Taq High Fidelity enzyme (Life Technologies 11304-011). Alternatively, pre-mixes were prepared by adding 0.5 mM MgCl$_2$ (25 mM), 12.5 ul 2×KAPA Fast HotStart Readymix (KAPA Biosystems KK5601), and 1.6 mg of acrylate-PEG-linker in 5.25 ul water.

To each pre-mix, 0.75 ul PCR primer mix (1 uM each of 2nd-strand/linear-amplification primers in Table 2 and 10 uM each of primers OE-PCR primers in Table 2) was added. 1 mg of thio-PEG-linker (Thiol-PEG-Thiol, MW 3,400, Laysan Bio) in 6 ul water was mixed quickly and added to the sample.

Hydrogels were allowed to form on ice for 15-20 minutes. In cases in which Platinum Taq polymerase was used, samples were thermocycled by heat-activation at 95 C (2 min), followed by 10 cycles of 95 C (30 sec)-68 C (2 min), 1 cycle of 95 C (30 sec)-58 C (30 sec)-68 C (2 min), 1 cycle of 95 C (30 sec)-56 C (30 sec)-68 C (2 min), and 22 cycles of 95 C (30 sec)-60 C (30 sec)-68 C (2 min). In cases in which KAPA Fast was used, samples were thermocycled by heat-activation at 95 C (1 min), followed by 10 cycles of 95 C (12 sec)-68 C (30 sec)-72 C (2 sec), 1 cycle of 95 C (12 sec)-58 C (20 sec)-72 C (2 sec), 1 cycle of 95 C (12 sec)-56 C (20 sec)-72 C (2 sec), and 22 cycles of 95 C (12 sec)-60 C (20 sec)-72 C (2 sec), and finally 72 C (5 sec). Samples were cooled to 4 C, and then stored at −20 C until further use.

Elution

Hydrogels were chemically degraded by adding 10 ul of a solution containing 290 mM KOH, 16 mM EDTA, and 29 mM DTT in water. Samples were centrifuged at 300×g for 2 minutes, and then incubated at 72 C for 5 minutes. 7 ul of stop solution (2% sulfuric acid, Qiagen 150343) was added. Alternatively, hydrogel was eluted by physically puncturing in 45 ul TE containing 10 mM EDTA, and 72 C incubation for 5 minutes.

6.8 ul of proteinase K solution containing 0.74% Tween-20 and 0.74 mg/ml proteinase K dissolved in water was added directly to samples (still in PDMS/bead wells). After mixing, reaction was incubated at 50 C for 25 min, followed by a 1:2 dilution in 10 mM Tris-HCl, pH 8. Eluted sample was then moved to a new plate, and then purified using Ampure XP beads (Beckman Coulter A63880) at a volume ratio of 0.65:1 beads:sample. 35 ul of 10 mM Tris-HCl, pH 8, was used to elute sample from beads. Sample was kept frozen at −20 C until further use.

NGS Library Preparation

DNA sequencing handles were added by further amplification. Ampure-eluted samples were added to a PCR mix containing final concentrations of 200 nM each of the primers 1'(long) and (12)-(5) (Table 2), 1× HiFi buffer, 200 uM per dNTP species, 1.5 mM MgSO$_4$, and 0.02 U/ul Platinum Taq HiFi polymerase. For oligo-blocking (Table 1), a final concentration of 3.3 uM each of the 3'-phosphate-capped oligos TTTTTTTTTTATTCCCATGGCGCGCCA/3Phos/ and TTTTTTTTTGGCGCGCCATGGGAATAA/3Phos/. Reactions were heat-activated at 95 C for 2 minutes, and then subjected to 20 cycles of 95 C (30 sec)-68 C (2 min). PCR product was subsequently purified with Ampure XP at a ratio of 0.65:1 beads:sample, and eluted into 10 mM Tris-HCl, pH 8. Individual samples were then barcoded by re-amplifying purified product in final reaction concentrations of 1×HiFi buffer, 200 nM per dNTP species, 2 mM MgSO$_4$, 0.02 U/ul Platinum Taq HiFi polymerase, and 200 nM each of the oligos AATGATACGGCGACCACCGA-GATCTACACTCTTTCCCTACACGACGCTCTTC-CGATC TAGCCACCCCACTTCTCTA and CAAGCA-GAAGACGGCATACGAGATXXXXXXXXGTGACTGG-AGTTCAGACGTGTGCT CTTCCGATCT (where XXXXXXX corresponds to the sample barcode), with 95 C (2 min) followed by 2 cycles of 95 C (30 sec)-60 C (30 sec)-68 C (2 min) and 8 cycles of 95 C (30 sec)-65 C (30 sec)-68 C (2 min). Libraries were size-purified with Ampure XP (0.7:1 beads:sample), eluted into 10 mM Tris-HCl pH 8, and stored at −20 C until sequencing on an Illumina MiSeq or HiSeq instrument.

Summary of Simulations

Simulations proceeded as follows. For all (discrete) PCR cycles t=1, 2, . . . , T, with T being the total PCR cycle number, the total molecules of monomer i were updated according to $$n_i(t+1) \rightarrow n_i(t) + \text{Binom}(n_i(t),p)$$

where $0 \leq p \leq 1$ is the rate of PCR doubling (as indicated in FIG. 11). Meanwhile, for all (discrete) PCR cycles t=1, 2, . . . , T, the expected rate of cross-link formation $r_{ij}(t)$ between every beacon i and target j was calculated according to the previously derived EQUATION 4

$$r_{ij}(t) \propto (t^{-d/2} e^{-\|\vec{x}_i - \vec{x}_j\|^2/8dDt}) n_i(t) n_j(t)$$

For a given total cross-link diversity Φ, expected cross-link diversities were then assigned $$\langle \phi_{ij}(t) \rangle = \Phi \frac{r_{ij}(t)}{\sum_{ijt} r_{ij}(t)}$$

The number of actual cross-linking events for every triplet (i,j,t) was then assigned randomly using Poisson statistics $$\phi_{ij}(t) \leftarrow \text{Pois}(\langle \phi_{ij}(t) \rangle)$$

The kth cross-linking event generated by the monomer-pair (i,j) at time t was then assigned a final abundance at time T using the iteration $$n_{ijk}(t+1) \leftarrow n_{ijk}(t) + \text{Binom}(n_{ijk}(t),p)$$

Each cross-link event's final read-abundance, given total read depth Ω (1000000 in FIG. 11), was then assigned $$w_{ijk}(T) \leftarrow \text{Pois}\left(\frac{\Omega n_{ijk}(T)}{\sum_{ijkt} n_{ijk}(T)}\right)$$

If $\omega_{ijk}(T) > 0$, the cross-linking event was considered detected. The cross-linking matrices used for FIG. 11 employ the total count of these cross-linking events as the input into the t-SNE algorithm (previously described) as the observed data values $P_{ij}$.

Summary of Analysis

Reads were de-multiplexed according to sample DNA barcode, and each UID (beacon α, target α, and β) was determined using the EASL algorithm. All UID's comprising a sequence of at least a 75%-majority of one base were discarded. For each β-UID, the beacon-target combination with the most reads was assigned. For each such pair, the total number of β-UID's with read-count of at least 2 was used as the elements of the association matrix. Individual α-UID's were only included in sample reconstructing if they were assigned two or more β-UID's. The association matrix was analyzed using the t-SNE embedding algorithm in two dimensions. Positions of determined beacons and targets are plotted in FIG. 12.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

---

What is claimed is:

1. A method for single cell mapping comprising
   (a) labeling template nucleic acid sequences in fixed cells with unique molecular identifiers (UID's), wherein the labeling comprises adding at least one α-UID to each template nucleic acid, thereby generating uniquely labeled template nucleic acids;
   (b) amplifying the labeled template nucleic acids using in situ amplification the amplification reaction also further concatenating individual amplified labeled template nucleic acids together such that each concatenation event results in incorporation of at least one unique β-UID, wherein the frequency of concatenation events between amplified labeled template nucleic acids is a function of a proximity of each individual labeled template nucleic acid to another labeled template nucleic acid; and
   (c) generating a spatially resolved physical mapping of each cell of the fixed cells by isolation and sequencing of the uniquely labeled concatenation events from (b).

2. The method of claim 1, wherein the nucleic acid is DNA.

3. The method of claim 2, wherein the DNA is complementary DNA (cDNA).

4. The method of claim 1, wherein the nucleic acid is RNA.

5. The method of claim 1, wherein the cell is fixed and permeabilized.

6. The method of claim 1, wherein the at least one UID is a completely random or computationally designed 10 to 50 mer between a gene-specific and adapter region of a primer used for reverse transcription.

7. The method of claim 1, further comprising cross-linking amplification products of steps (b) and/or (c).

8. The method of claim 7, wherein the cross-linking further comprises an additional UID-labeling step.

9. The method of claim 7, wherein the cross-linking comprises overlap extension polymerase chain reaction.

10. The method of claim 7, wherein the cross-linking comprises associating multiple amplification products with ligase or capture beads.

11. The method of claim 1, wherein the amplification comprises thermocycling or isothermal amplification.

12. The method of claim 1, wherein the amplification occurs in solution, in a hydrogel, or on a solid support.

* * * * *

UNITED STATES PATENT AND TRADEMARK OFFICE
CERTIFICATE OF CORRECTION

PATENT NO. : 10,655,173 B2
APPLICATION NO. : 15/030154
DATED : May 19, 2020
INVENTOR(S) : Feng Zhang et al.

It is certified that error appears in the above-identified patent and that said Letters Patent is hereby corrected as shown below:

On the Title Page

Item (56), in Column 2, under "Foreign Patent Documents", Line 5, delete "WO 9703211 A1 1/1999" and insert -- WO 9703211 A1 1/1997 --, therefor.

Item (56), in Column 2, under "Other Publications", Line 3, delete "Patentabiity" and insert -- Patentability --, therefor.

On the page 2, in Column 2, under "Other Publications", Line 1, delete "Microsopy:" and insert -- Microscopy: --, therefor.

On the page 2, in Column 2, under "Other Publications", Line 10, delete ""Digitial" and insert -- "Digital --, therefor.

In the Specification

In Column 9, Line 9, delete "$P_{ij} = n_{ij} / \Sigma_i n_{ij}, P_{j|i} = n_{ij} / \Sigma_j n_{ij},$" and insert -- $P_{i|j}=n_{ij} / \Sigma_i n_{ij}, P_{j|i}=n_{ij} / \Sigma_j n_{ij}$, --, therefor.

In Column 10, Line 37, delete "$N_{crit},$" and insert -- $N_{crit,}(\ell)$ --, therefor.

In Column 11, Line 14, delete "t≥τ$_{min}$" and insert -- $t \geq t_{min}$ --, therefor.

In Column 11, Line 39, delete "α(T)," and insert -- $a(T)$, --, therefor.

Signed and Sealed this
Sixth Day of October, 2020

Andrei Iancu
*Director of the United States Patent and Trademark Office*

CERTIFICATE OF CORRECTION (continued)
U.S. Pat. No. 10,655,173 B2

In Column 11, Lines 45-55, delete "

$$a(T) = \frac{\int_{\tau_{min}}^{T} \tau^{-d/2} e^{2A\tau} e^{A(t-\tau)} d\tau}{\int_{\tau_{min}}^{T} e^{2A\tau} e^{A(T-\tau)} (\tau^{-d/2} + \rho(8\pi dD)^{d/2})) d\tau}$$

$$= \left(1 + \frac{\int_{\tau_{min}}^{T} \rho e^{A\tau} (8\pi dD)^{d/2} d\tau}{\int_{\tau_{min}}^{T} e^{A\tau} \tau^{-d/2} d\tau}\right)^{-1}$$

$$= \left(1 + \frac{\rho(e^{AT} - e^{A\tau_{min}})(8\pi dD)^{d/2}}{A \int_{\tau_{min}}^{T} e^{A\tau} \tau^{-d/2} d\tau}\right)^{-1}$$

"

and insert --

$$a(T) = \frac{\int_{\tau_{min}}^{T} \tau^{-d/2} e^{2A\tau} e^{A(T-\tau)} d\tau}{\int_{\tau_{min}}^{T} e^{2A\tau} e^{A(T-\tau)} (\tau^{-d/2} + \rho(8\pi dD)^{d/2})) d\tau}$$

$$= \left(1 + \frac{\int_{\tau_{min}}^{T} \rho e^{A\tau} (8\pi dD)^{d/2} d\tau}{\int_{\tau_{min}}^{T} e^{A\tau} \tau^{-d/2} d\tau}\right)^{-1}$$

$$= \left(1 + \frac{\rho(e^{AT} - e^{A\tau_{min}})(8\pi dD)^{d/2}}{A \int_{\tau_{min}}^{T} e^{A\tau} \tau^{-d/2} d\tau}\right)^{-1}$$

--, therefor.

In Column 12, Line 9, delete "Prob(τ) ∝ $e^{-2A\tau} dt$" and insert -- Prob(τ) ∝ $e^{-2A\tau} d\tau$ --, therefor.

In Column 12, Line 36, delete "α<<A" and insert -- α'<<A --, therefor.

In Column 14, Line 49, delete "cells," and insert -- cells. --, therefor.

In Column 15, Lines 29-30, delete "fluorcoumanin," and insert -- fluoro coumarin, --, therefor.

In Column 15, Line 30, delete "daunomyc in," and insert -- daunomycin, --, therefor.

In Column 15, Line 30, delete "distamyc in" and insert -- distamycin --, therefor.

In Column 15, Line 31, delete "chromomyc in," and insert -- chromomycin, --, therefor.

In Columns 17-18, Lines 36-37, delete ""olignucleotide"" and insert -- "oligonucleotide" --, therefor.

In Column 19, Line 25, delete "Hoogstein" and insert -- Hoogsteen --, therefor.

In Column 21, Lines 48-49, delete "pyriylalanine," and insert -- pyridylalanine, --, therefor.

In Column 22, Line 28, delete "phosphoimager." and insert -- phosphorimager. --, therefor.

CERTIFICATE OF CORRECTION (continued)
U.S. Pat. No. 10,655,173 B2

In Column 22, Line 57, delete "7-amino-4-trifluoromethylcouluarin" and insert -- 7-amino-4-trifluoromethylcoumarin --, therefor.

In Column 23, Lines 7-8, delete "4-methylumbelliferoneortho cresolphthalein;" and insert -- 4-methylumbelliferone ortho cresolphthalein; --, therefor.

In Column 23, Lines 17-18, delete "N,N,N',N' tetramethyl-6-carboxyrhodamine" and insert -- N,N,N',N'-tetramethyl-6-carboxyrhodamine --, therefor.

In Column 23, Lines 21-22, delete "phthalo cyanine;" and insert -- phthalocyanine; --, therefor.

In Column 23, Line 22, delete "naphthalo cyanine" and insert -- naphthalocyanine. --, therefor.

In Column 23, Line 26, delete "Colormetric" and insert -- Colorimetric --, therefor.

In Column 27, Line 10, delete "55 C" and insert -- 55° C. --, therefor.

In Column 27, Line 29, delete "80 C," and insert -- 80° C., --, therefor.

In Column 27, Line 30, delete "80 C" and insert -- 80° C. --, therefor.

In Column 27, Line 34, delete "37 C," and insert -- 37° C., --, therefor.

In Column 27, Line 40, delete "37 C." and insert -- 37° C. --, therefor.

In Column 27, Line 62, delete "60 C" and insert -- 60° C. --, therefor.

In Column 27, Line 62, delete "42 C" and insert -- 42° C. --, therefor.

In Column 27, Line 63, delete "4 C" and insert -- 4° C. --, therefor.

In Column 28, Line 2, delete "37 C" and insert -- 37° C. --, therefor.

In Column 28, Line 23, delete "95 C" and insert -- 95° C. --, therefor.

In Column 28, Line 24, delete "95 C" and insert -- 95° C. --, therefor.

In Column 28, Line 24, delete "68 C" and insert -- 68° C. --, therefor.

In Column 28, Line 25, delete "95 C" and insert -- 95° C. --, therefor.

In Column 28, Line 25, delete "58 C" and insert -- 58° C. --, therefor.

In Column 28, Line 25, delete "68 C" and insert -- 68° C. --, therefor.

In Column 28, Line 26, delete "95 C" and insert -- 95° C. --, therefor.

CERTIFICATE OF CORRECTION (continued)
U.S. Pat. No. 10,655,173 B2

In Column 28, Line 26, delete "56 C" and insert -- 56° C. --, therefor.

In Column 28, Line 26, delete "68 C" and insert -- 68° C. --, therefor.

In Column 28, Line 27, delete "95 C" and insert -- 95° C. --, therefor.

In Column 28, Line 27, delete "60 C" and insert -- 60° C. --, therefor.

In Column 28, Line 27, delete "68 C" and insert -- 68° C. --, therefor.

In Column 28, Line 29, delete "95 C" and insert -- 95° C. --, therefor.

In Column 28, Lines 29-30, delete "95 C" and insert -- 95° C. --, therefor.

In Column 28, Line 30, delete "68 C" and insert -- 68° C. --, therefor.

In Column 28, Line 30, delete "72 C" and insert -- 72° C. --, therefor.

In Column 28, Line 30, delete "95 C" and insert -- 95° C. --, therefor.

In Column 28, Line 31, delete "58 C" and insert -- 58° C. --, therefor.

In Column 28, Line 31, delete "72 C" and insert -- 72° C. --, therefor.

In Column 28, Line 31, delete "95 C" and insert -- 95° C. --, therefor.

In Column 28, Lines 31-32, delete "56 C" and insert -- 56° C. --, therefor.

In Column 28, Line 32, delete "72 C" and insert -- 72° C. --, therefor.

In Column 28, Line 32, delete "95 C" and insert -- 95° C. --, therefor.

In Column 28, Lines 32-33, delete "60 C" and insert -- 60° C. --, therefor.

In Column 28, Line 33, delete "72 C" and insert -- 72° C. --, therefor.

In Column 28, Line 33, delete "72 C" and insert -- 72° C. --, therefor.

In Column 28, Line 34, delete "4 C," and insert -- 4° C., --, therefor.

In Column 28, Line 34, delete "-20 C" and insert -- -20° C. --, therefor.

In Column 28, Line 40, delete "72 C" and insert -- 72° C. --, therefor.

In Column 28, Line 43, delete "72 C" and insert -- 72° C. --, therefor.

CERTIFICATE OF CORRECTION (continued)
U.S. Pat. No. 10,655,173 B2

In Column 28, Line 48, delete "50 C" and insert -- 50° C. --, therefor.

In Column 28, Line 54, delete "-20 C" and insert -- -20° C. --, therefor.

In Column 28, Line 65, delete "95 C" and insert -- 95° C. --, therefor.

In Column 28, Line 66, delete "95 C" and insert -- 95° C. --, therefor.

In Column 28, Line 66, delete "68 C" and insert -- 68° C. --, therefor.

In Column 29, Line 8, delete "CGATC TAGCCACCCCACTTCTCTA" and insert -- CGATCTAGCCACCCCACTTCTCTA --, therefor.

In Column 29, Line 10, delete "GCT CTTCCGATCT" and insert -- GCTCTTCCGATCT --, therefor.

In Column 29, Line 11, delete "95 C" and insert -- 95° C. --, therefor.

In Column 29, Line 12, delete "95 C" and insert -- 95° C. --, therefor.

In Column 29, Line 12, delete "60 C" and insert -- 60° C. --, therefor.

In Column 29, Line 13, delete "68 C" and insert -- 68° C. --, therefor.

In Column 29, Line 13, delete "95 C" and insert -- 95° C. --, therefor.

In Column 29, Line 13, delete "65 C" and insert -- 65° C. --, therefor.

In Column 29, Line 14, delete "68 C" and insert -- 68° C. --, therefor.

In Column 29, Line 16, delete "-20 C" and insert -- -20° C. --, therefor.

In the Claims

In Column 41, Line 27, in Claim 1, after "comprising" insert -- : --.

In Column 41, Line 34, in Claim 1, after "situ amplification" insert -- , --.